(12) United States Patent
Urbanski et al.

(10) Patent No.: US 12,207,836 B2
(45) Date of Patent: Jan. 28, 2025

(54) METHODS AND DEVICES FOR PUNCTURING TISSUE

(71) Applicant: Boston Scientific Medical Device Limited, Ballybrit (IE)

(72) Inventors: John Paul Urbanski, Toronto (CA); Matthew Dicicco, Guelph (CA); Yun Uhm, Toronto (CA); Neil Godara, Milton (CA); David Rees, Toronto (CA); James Klein, Toronto (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 163 days.

(21) Appl. No.: 16/346,404

(22) PCT Filed: Oct. 31, 2017

(86) PCT No.: PCT/IB2017/056777
§ 371 (c)(1),
(2) Date: Apr. 30, 2019

(87) PCT Pub. No.: WO2018/083599
PCT Pub. Date: May 11, 2018

(65) Prior Publication Data
US 2020/0060710 A1   Feb. 27, 2020

Related U.S. Application Data

(60) Provisional application No. 62/415,913, filed on Nov. 1, 2016.

(51) Int. Cl.
*A61B 17/3205*   (2006.01)
*A61B 17/34*   (2006.01)
(Continued)

(52) U.S. Cl.
CPC ...... *A61B 17/3205* (2013.01); *A61B 17/3417* (2013.01); *A61B 90/39* (2016.02);
(Continued)

(58) Field of Classification Search
CPC .......... A61B 17/32053; A61B 17/3205; A61B 90/39; A61B 17/3417; A61B 2090/3966;
(Continued)

(56) References Cited

U.S. PATENT DOCUMENTS

| 175,254 A | 3/1876 | Oberly |
| 827,626 A | 7/1906 | Gillet |

(Continued)

FOREIGN PATENT DOCUMENTS

| CN | 105682726 | 1/2020 |
| EP | 3064246 A1 | 9/2016 |

(Continued)

OTHER PUBLICATIONS

Patent Corporation Treaty, International Search Report for PCT Application No. PCT/IB2017/056777, mailed Mar. 27, 2018.
(Continued)

*Primary Examiner* — Richard G Louis
(74) *Attorney, Agent, or Firm* — Nelson Mullins Riley & Scarborough LLP

(57) ABSTRACT

A method and system are disclosed for puncturing tissue, comprising a puncture device for puncturing tissue and a supporting member for supporting the puncture device. The puncture device is capable of being insertable within the supporting member and being selectively usable in co-operation therewith during a portion of a procedure for puncturing tissue and wherein the puncture device is usable independently therefrom during another portion of the procedure.

20 Claims, 18 Drawing Sheets

(51) Int. Cl.
  *A61B 90/00* (2016.01)
  *A61M 29/00* (2006.01)
  *A61B 17/00* (2006.01)
  *A61B 17/22* (2006.01)
  *A61B 18/00* (2006.01)

(52) U.S. Cl.
  CPC .................. *A61M 29/00* (2013.01); *A61B 2017/00247* (2013.01); *A61B 2017/22044* (2013.01); *A61B 2018/00351* (2013.01); *A61B 2018/00601* (2013.01); *A61B 2090/3966* (2016.02)

(58) Field of Classification Search
  CPC ........... A61B 2017/00247; A61B 2017/22044; A61B 2018/00351; A61B 2018/00601; A61B 2017/00331; A61B 2090/08021; A61B 17/3478; A61B 2017/00252; A61B 2018/00357; A61B 2018/00839; A61B 2018/144; A61B 18/1492; A61M 29/00
  See application file for complete search history.

(56) References Cited

U.S. PATENT DOCUMENTS

| | | |
|---|---|---|
| 848,711 A | 4/1907 | Daniel |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Langberg |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |

(56) References Cited

U.S. PATENT DOCUMENTS

| | | |
|---|---|---|
| 6,228,076 B1 | 5/2001 | Winston et al. |
| 6,245,054 B1 | 6/2001 | Fuimaono et al. |
| 6,267,758 B1 | 7/2001 | Daw et al. |
| 6,270,476 B1 | 8/2001 | Santoianni |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,048,733 B2 | 5/2006 | Hartley et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 8,900,193 B2 * | 12/2014 | Paul .................. A61B 17/3478 604/164.12 |
| 9,072,872 B2 | 7/2015 | Asleson et al. |
| 9,757,541 B2 | 9/2017 | Haarer |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2001/0051790 A1 | 12/2001 | Parker |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0171642 A1 * | 9/2003 | Schock .................. A61M 25/09 600/18 |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0149062 A1 | 7/2005 | Carroll |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0149995 A1 | 6/2007 | Quinn et al. |

(56) References Cited

U.S. PATENT DOCUMENTS

| | | |
|---|---|---|
| 2007/0167775 A1 | 7/2007 | Kochavi et al. |
| 2007/0208256 A1 | 9/2007 | Marilla |
| 2007/0225681 A1 | 9/2007 | House |
| 2007/0270751 A1* | 11/2007 | Stangenes ........ A61B 17/00234 |
| | | 604/164.1 |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0243081 A1 | 10/2008 | Nance et al. |
| 2008/0275439 A1 | 11/2008 | Francischelli et al. |
| 2008/0294111 A1* | 11/2008 | Tal .................... A61M 25/0606 |
| | | 604/165.01 |
| 2009/0005780 A1* | 1/2009 | Kato .................. A61B 18/1492 |
| | | 606/50 |
| 2009/0105654 A1* | 4/2009 | Kurth ............... A61M 25/09041 |
| | | 604/170.03 |
| 2009/0105742 A1 | 4/2009 | Kurth et al. |
| 2009/0125097 A1* | 5/2009 | Bruszewski ........ A61M 25/065 |
| | | 623/1.23 |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2009/0281557 A1* | 11/2009 | Sander ............... A61B 17/3468 |
| | | 606/151 |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0249908 A1 | 11/2010 | Chau et al. |
| 2011/0046619 A1 | 2/2011 | Ducharme |
| 2011/0087211 A1* | 4/2011 | Kulesa ............... A61B 18/1492 |
| | | 700/12 |
| 2011/0087261 A1* | 4/2011 | Wittkampf ......... A61B 17/3478 |
| | | 606/185 |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0196233 A1 | 8/2011 | Martinez-Arraras |
| 2012/0109079 A1 | 5/2012 | Asleson et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0072958 A1* | 3/2013 | Ressemann ........... A61M 29/00 |
| | | 606/199 |
| 2013/0123827 A1* | 5/2013 | Kellerman ......... A61B 17/3468 |
| | | 606/185 |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0012228 A1 | 1/2014 | Jabba et al. |
| 2014/0107681 A1 | 4/2014 | Davies et al. |
| 2014/0206987 A1 | 7/2014 | Urbanski et al. |
| 2014/0296769 A1 | 10/2014 | Hyde et al. |
| 2014/0371676 A1* | 12/2014 | Leeflang ............ A61B 17/3423 |
| | | 604/164.1 |
| 2015/0133989 A1* | 5/2015 | Lubock .............. A61B 17/0057 |
| | | 606/200 |
| 2015/0157353 A1 | 6/2015 | Lenker et al. |
| 2015/0374930 A1* | 12/2015 | Hyde .................. A61M 5/3291 |
| | | 604/239 |
| 2016/0073960 A1* | 3/2016 | Jung .................... A61B 5/6858 |
| | | 600/374 |
| 2016/0175009 A1* | 6/2016 | Davies ............... A61B 17/3478 |
| | | 606/47 |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| EP | 3064246 | 10/2020 |
| JP | 2002532164 A | 10/2002 |
| JP | 2011206179 A | 10/2011 |
| JP | 2015504328 A | 2/2015 |
| JP | 2016530928 A | 10/2016 |
| WO | 2014182969 | 11/2014 |

OTHER PUBLICATIONS

Patent Corporation Treaty, Written Opinion for PCT Application No. PCT/IB2017/056777, mailed Mar. 27, 2018.
Patent Corporation Treaty, International Search Report for co-pending PCT Application No. PCT/IB2019/053745, mailed Sep. 18, 2019.
Patent Corporation Treaty, Written Opinion for co-pending PCT Application No. PCT/IB2019/053745, mailed Sep. 18, 2019.
Corresponding European Application, European Search Report, dated Jun. 8, 2020.
Corresponding Japanese Application, Office Action, dated Aug. 13, 2021.
Corresponding European Application, Examiner Search Report, dated Jul. 8, 2021.
Corresponding European Application, Extended Examiner Search Report, dated Jun. 8, 2020.

* cited by examiner

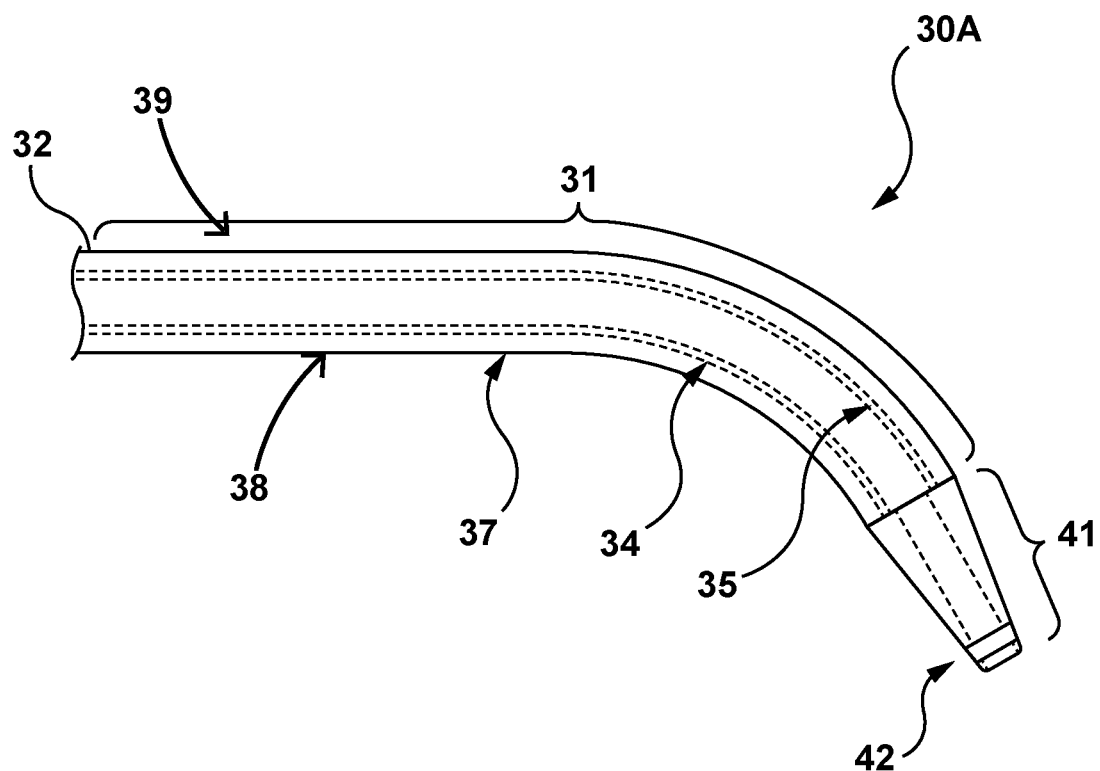
FIG. 1D
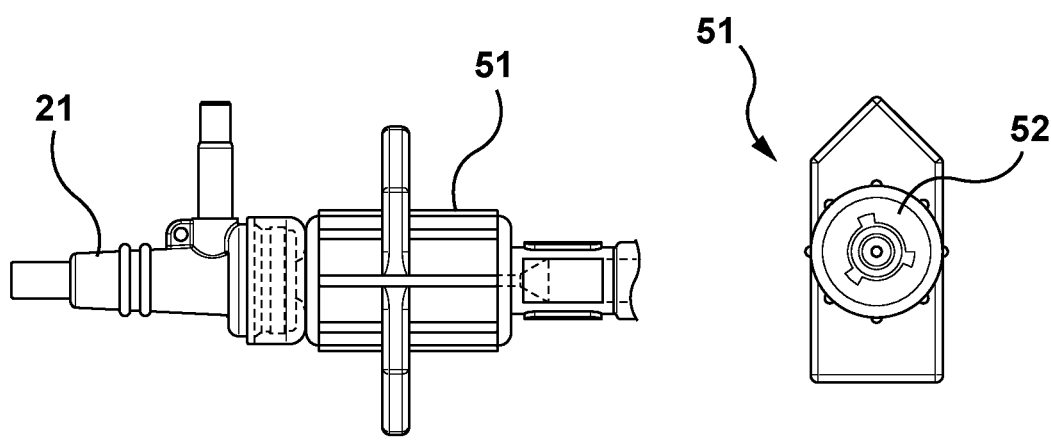
FIG. 1E
FIG. 1F

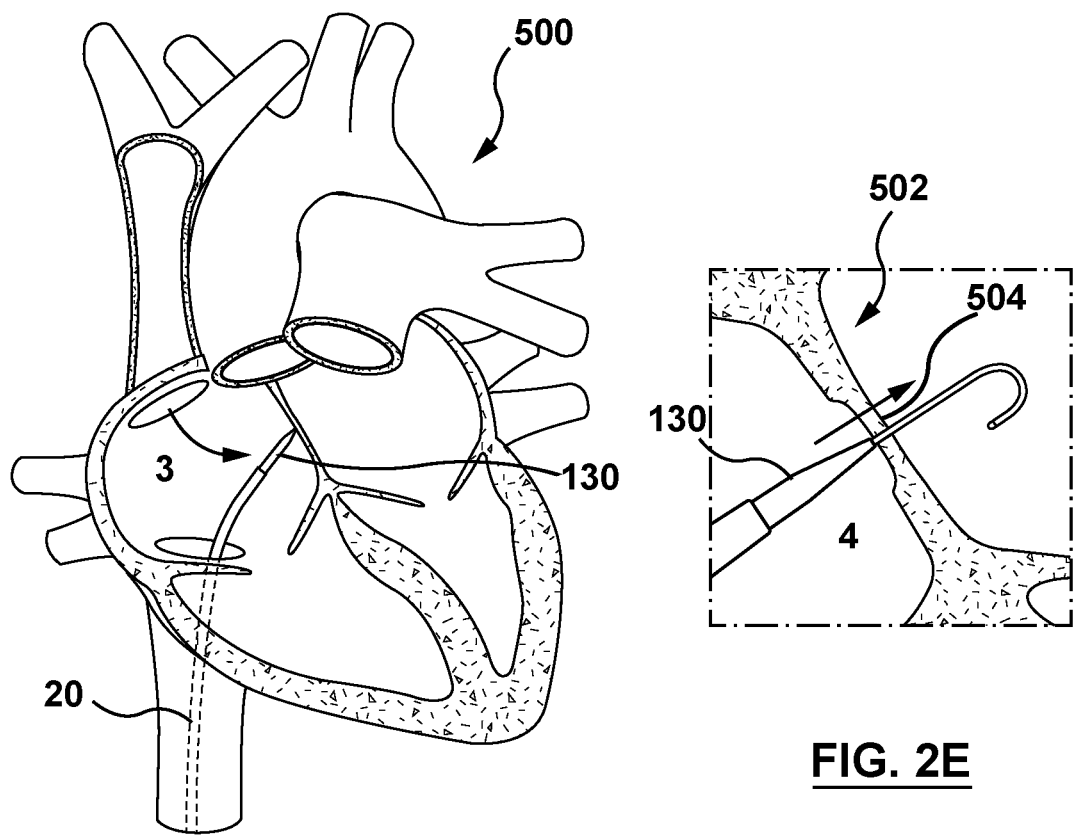
FIG. 2D
FIG. 2E
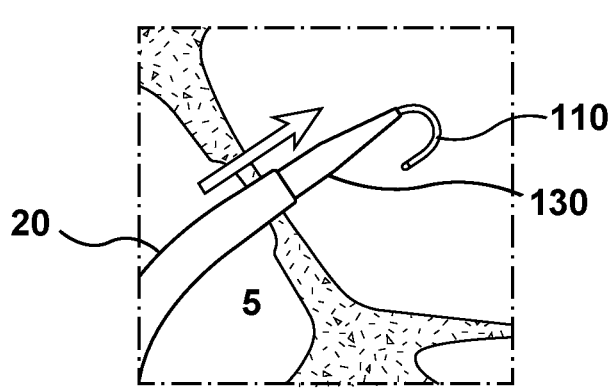
FIG. 2F
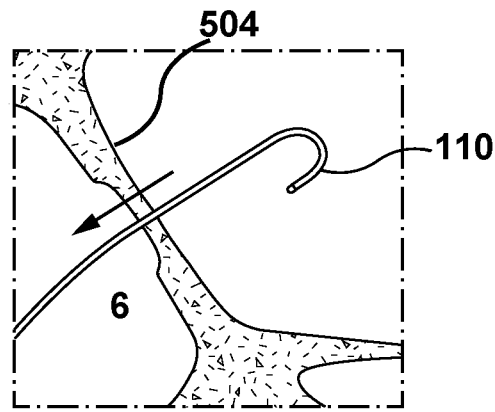
FIG. 2G

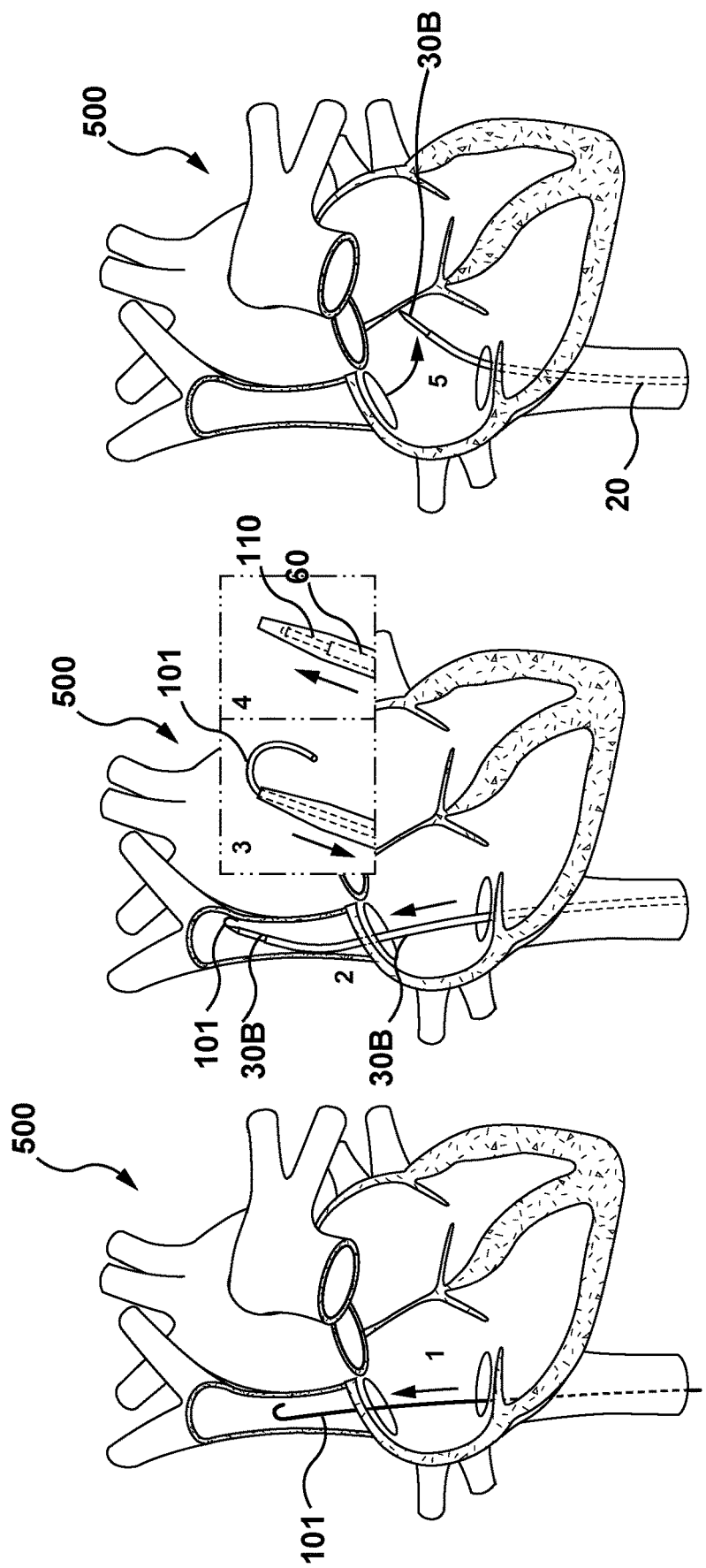

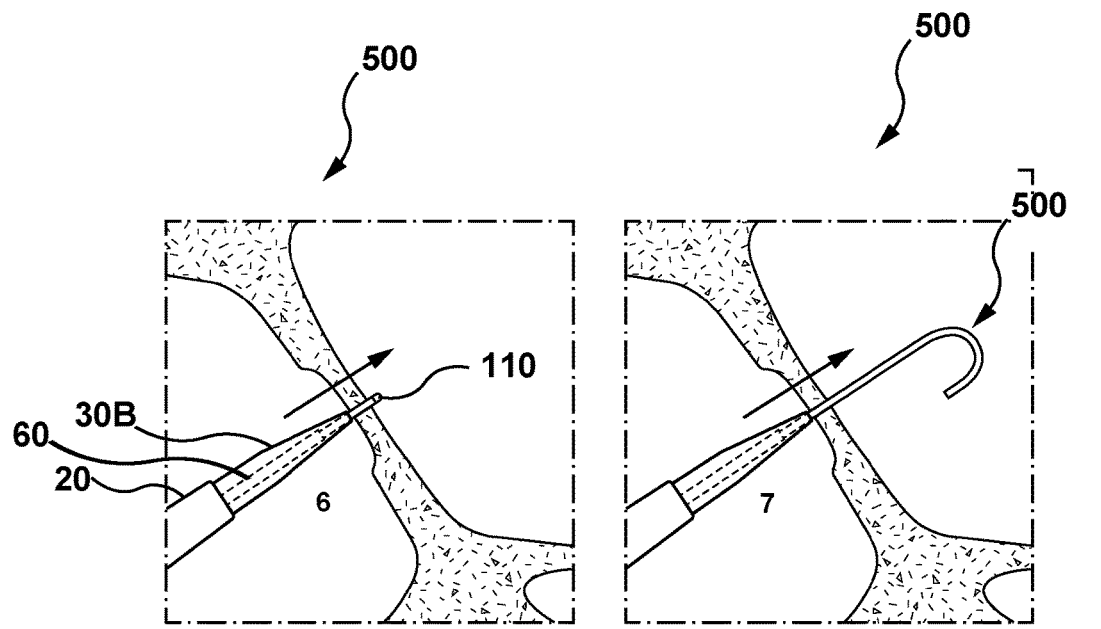
FIG. 6E  FIG. 6F
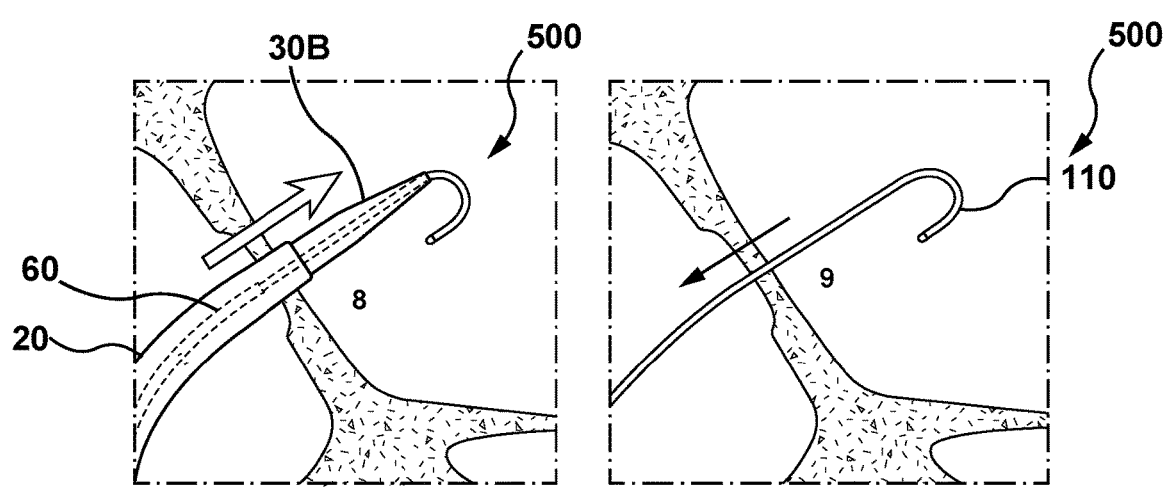
FIG. 6G  FIG. 6H

METHODS AND DEVICES FOR PUNCTURING TISSUE

TECHNICAL FIELD

The disclosure relates to systems and methods for creating a puncture in tissue. More specifically, the disclosure relates to systems and methods for creating a puncture using an assembly including a puncture device and a supporting member.

BRIEF DESCRIPTION OF THE DRAWINGS

In order that the invention may be readily understood, embodiments of the invention are illustrated by way of examples in the accompanying drawings, in which:

FIGS. 1C and 1D show a dilator comprising a reinforcing member in accordance with embodiments of the present invention;

FIG. 1E shows a locking mechanism for enabling coupling of a sheath and dilator during use, in accordance with an embodiment of the present invention;

FIG. 1F is an illustration of a dilator hub with keys for enabling locking of the dilator hub to the sheath hub, in accordance with an embodiment of the present invention;

FIGS. 2B-2G illustrate steps of a method of performing a transseptal procedure, in accordance with an embodiment of the present invention;

FIGS. 6B-6H illustrate steps of a method of performing a transseptal procedure, in accordance with an alternate embodiment of the present invention.

DETAILED DESCRIPTION

Figure 1A:
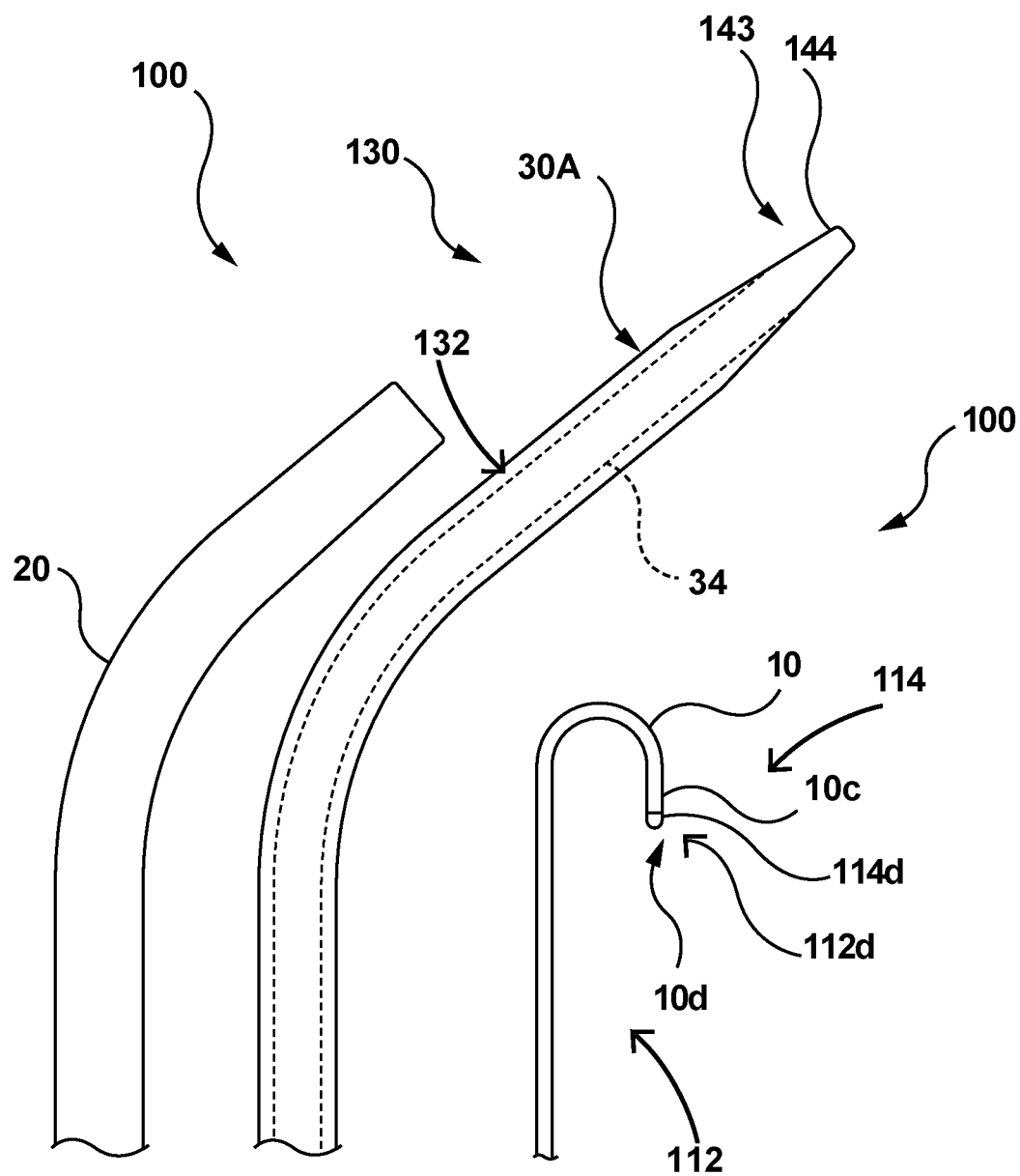
FIGS. 1A and 1B are illustrations of a transseptal assembly in accordance with embodiments of the present invention.

In order to carry out a transseptal procedure, it is necessary to gain access to the heart. Access may be obtained (specifically to the right atrium of the heart) from a superior approach (by gaining access to the heart from an access point above the heart, for example from the jugular vein through the superior vena cava), or alternatively access may be obtained from the femoral or inferior approach (by gaining access to the heart from an access point below the heart, for example from the femoral vein through the inferior vena cava). Once access is obtained into the right atrium, a puncture device is utilized in order to puncture through tissue for example across a septum of the heart to gain access from the right atrium into the left atrium of the heart.

Some conventional transseptal procedures, for example some that use the inferior approach to gain access to the heart, use a needle in order to carry out a transseptal puncture. Certain limitations may be associated with the use of needles or other rigid devices for carrying out a transseptal puncture procedure.

These limitations may include one or more of: (1) need for a separate exchange wire to gain access to the SVC resulting in multiple device exchanges on the right side. (2) the use of a needle may require multiple device exchanges in order to complete the procedure; (3) difficulty in correcting placement of the puncture device after insertion within the right atrium if the target location on the fossa is missed; (4) there may be a lack of repeatability for certain aspects of the procedure for completing the puncture in an effective and timely manner, (5) the puncture device may not provide sufficient atraumacity and may result in excessive force being applied to puncture tissue resulting in damage to tissue; (6) possible risk of trauma to the structures within the left atrium following puncture due to the force of advancement; (7) there may be a lack of adequate anchoring after puncture to maintain access; (8) need for an additional exchange on the left side requiring removal of the puncture device and advancement of another wire (such as a pigtail wire) to facilitate anchoring, and/or (9) trackability to allow additional devices to be tracked over the wire once in the left side.

The inventors of the present invention have discovered systems and methods that attempt to overcome the limitations associated with prior art systems.

In some such examples, where a sharp mechanical needle is used, the device may not be sufficiently atraumatic to minimize the risk of damage to tissue, and the mechanical needle does not provide adequate anchoring after puncture.

In other examples, where an energy based needle such as an RF needle is used, the RF needle may require multiple device exchanges, and there may be lack of repeatability for one or more steps in the procedure, leading to increased procedural time and/or inefficiency. Furthermore, the RF needle may not provide adequate anchoring after puncture.

In one broad aspect, the present inventors have discovered systems and methods that provide an RF wire and devices for supporting the same, in order to facilitate a transseptal puncture, for example using the inferior approach. The systems and methods of the present invention attempt to overcome limitations associated with conventional transseptal systems that utilize needles in order to complete the transseptal puncture procedure. Some such conventional transseptal procedures that require the use of a needle, use the inferior approach to gain access to the heart, in order to carry out the transseptal puncture.

Current rigid mechanical needles provide a sharp tip in order to puncture tissue. Such mechanical needles may have several limitations which may include one or more of: (1) the sharp mechanical needle may not provide sufficient artramaticity and may result in excessive force being applied to puncture tissue resulting in damage to tissue; (2) possibly risk of trauma to the structures within the left atrium following puncture due to the force of advancement (3) need for an additional exchange on the left side requiring removal of the needle and advancement of another wire (such as a pigtail wire) to facilitate anchoring, and/or trackability to allow additional devices to be tracked over the wire once in left side Furthermore, current rigid energy-based devices used for puncturing tissue may also have one or more of the several limitations noted herein above.

Inventors of the present invention have developed various embodiments of a novel system and method that involves providing, in one broad aspect, a puncture device having two components: (1) a separate puncturing component or member and (2) a substantially rigid and/or stiff supporting member that is that is removable or independent from the puncturing component or member, allowing the supporting member to be used selectively with the puncturing device.

In some examples, the (1) separate puncturing component or member comprises a substantially flexible tissue puncturing component or member. In some such examples, the separate substantially flexible tissue puncturing component or member may be substantially atraumatic. Furthermore, in some examples, the separate substantially flexible tissue puncturing component or member may have a relatively sharp component such as a relatively sharp distal tip component.

In some embodiments, the Inventors of the present invention have developed a novel system that involves providing a stiff energy-based puncture device having two components: (1) a flexible [atraumatic] energy based puncturing device or member such as a radiofrequency (RF) wire and (2) a stiff supporting member such as a reinforcing member, that is removable or independent from the flexible energy based puncturing device.

In another broad aspect, a novel assembly is provided including a decoupled needle assembly comprising: a (1) a substantially flexible tissue puncturing member or component for puncturing tissue (which may additionally be substantially atraumatic), and (2) a substantially stiff needle shaft for supporting the puncturing member that is selectively usable with it. In some such embodiments, the needle shaft is substantially rigid to provide force transmission capabilities but lacks tissue puncturing capabilities (in other words the needle shaft is still sufficiently atraumatic so as not to puncture tissue).

Thus, some embodiments of the present invention include separating the components of an puncture device into two independently operable components that form an assembly and thereby provide two separate and independent functionalities, (i) that of puncturing tissue with a substantially flexible and/or atraumatic component (such as a flexible energy delivery device but not limited thereto) and (ii) that of supporting the substantially atraumatic puncturing component using a substantially stiff or rigid needle shaft. Such embodiments provide one or more advantages not previously realized or realizable using existing systems.

The advantages may include one or more of: (i) providing a substantially flexible and/or atraumatic puncture device (such as an energy delivery puncture device) while (ii) providing a substantially rigid supporting member such as a rigid needle shaft for supporting the substantially atraumatic puncture device:

enabling the substantially flexible puncture device to be usable separately from the substantially rigid supporting member to enable the substantially flexible puncture device to function as an exchange wire;

enabling the substantially flexible puncture device to be usable in co-operation with the substantially rigid supporting member for example by allowing the substantially rigid supporting member to be advanced over the substantially flexible puncture device to allow sufficient force transmission and/or torque to be transmitted to the distal tip of the assembly (for example, to facilitate the drop down procedure to locate the fossa as described herein below) and to provide adequate support to facilitate puncture (using the substantially flexible puncture device and to facilitate crossing with the substantially flexible puncture device);

enabling use of the substantially flexible puncture device to be usable separately from the substantially rigid supporting member to enable the substantially flexible puncture device to additionally function as a puncturing device to puncture tissue while minimizing the risk of damage to tissue (such as for example, non-punctured tissue) during puncture and to facilitate crossing using the substantially flexible puncture device;

enabling the substantially flexible puncture device to be usable separately from the substantially rigid supporting member to minimize risk of damage to tissue, for example on the left side of the heart once access has been obtained, for example in a transseptal puncture by providing an atraumatic tip and reducing the amount of force needed to puncture tissue, for example, by using delivery of energy;

enabling the substantially rigid supporting member such as the needle shaft to be removed or retracted to enable repositioning of the assembly against the target tissue site by allowing the substantially flexible (which may additionally be atraumatic) energy delivery puncture device to be usable independently from the substantially rigid supporting member to be re-tracked into a desired vasculature to enable the substantially rigid support member to be re-advanced over the substantially flexible energy delivery device for example, to repeat a drop down procedure in a transseptal puncture for positioning the assembly against the fossa;

enabling the substantially rigid support member such as the needle shaft to be removed after puncturing, allowing the substantially atraumatic energy delivery device to be usable independently from the substantially rigid supporting member to provide anchoring after puncture using the puncturing device by allowing it to remain positioned on the left side of the heart to maintain access to the left side of heart, and to additionally allow for track-ability of additional devices over the puncture device for guidance into the left side of the heart.

The system of the present invention provides several advantages corresponding to the aforementioned problems where providing a substantially flexible atraumatic puncture device such as an RF wire in combination with a separate or independent support member such as a substantially rigid needle shaft or a reinforcing member (for example that forms a substantially rigid needle shaft) that is selectively usable with the substantially flexible atraumatic puncture device, provides the following advantages:

a) the system enables the reinforcing member to be advanced over the RF wire allowing the RF wire to function as an exchange wire, which may help streamline work flow and reduce the number of device exchanges on the right side of the heart, to help reduce procedural time and complexity;

b) the system enables repeatability of the drop down procedure by enabling partial removal or partial retraction or withdrawal of the reinforcing member to enable re-positioning and/or re-advancement of the RF puncturing device such as the RF wire within the SVC without requiring an additional exchange;

c) the system additionally enables removal of the reinforcing member after puncture: (i) to allow the RF wire to remain positioned within the left atrium to help avoid the risk of trauma; and/or (ii) to enable anchoring within the left side, without requiring an additional exchange, for example to enhance procedural safety or efficiency; and/or (iii) to allow the RF wire to be maintained within the left atrium for trackability or in other words to assist in subsequent device delivery or subsequently tracking devices over the RF wire. The benefit of minimizing exchanges, in addition to reducing time/steps, is minimizing risk of infection. This is particularly important on the left side of the heart, where any unnecessary exchanges may lead to increased risk of embolism, strokes, etc.

As described above, in some embodiments, the substantially flexible tissue puncturing component or member is selectively usable with the substantially rigid supporting member. In some such examples, selectively usable refers to the substantially flexible energy based puncturing device being capable of being detachably usable or selectively insertable within or detachably coupled to the supporting member in order to be used with the supporting member during a portion of the procedure and being removable, detachable or retractable from the supporting member, or otherwise usable independently from the supporting member during another portion of the procedure.

In one broad aspect embodiments of the present invention comprise a needle assembly for puncturing tissue and enhancing procedural efficiency by facilitating exchange and positioning, the needle assembly comprising: a puncture device for puncturing tissue; and a supporting member for supporting the puncture device; Wherein the puncture device is capable of being insertable within the supporting member and being selectively usable in co-operation therewith during a portion of a procedure for puncturing tissue and wherein the puncture device is usable independently therefrom during another portion of the procedure.

In another broad aspect, embodiments of the present invention comprise an assembly for puncturing tissue, the assembly comprising: a substantially flexible puncture device for puncturing tissue, and a supporting member for supporting the substantially flexible puncturing device; Wherein the substantially flexible puncture device is capable of being selectively insertable within the supporting member to be selectively usable in co-operation therewith during a portion of a procedure for puncturing tissue and wherein the substantially flexible puncture device is usable independently therefrom during another portion of the procedure, in order to puncture tissue while facilitating exchange and positioning.

In another broad aspect, embodiments of the present invention comprise an assembly for puncturing tissue, the assembly comprising: a substantially flexible energy delivery puncture device for puncturing tissue via delivery of energy; and a supporting member for supporting the substantially flexible energy delivery puncture device; Wherein the substantially flexible energy delivery puncture device is capable of being selectively insertable within the supporting member to be selectively usable in co-operation therewith during a portion of a procedure for puncturing tissue and wherein the substantially flexible energy delivery puncture device is usable independently therefrom during another portion of the procedure, in order to facilitate exchange and positioning while providing substantially atraumatic puncture of tissue.

In another broad aspect, embodiments of the present invention comprise a needle assembly for puncturing tissue, the needle assembly comprising: a flexible puncture device for puncturing tissue; and a stiffening member for supporting the puncture device; Wherein the puncture device is capable of being selectively usable in co-operation with the stiffening member during a portion of the procedure and wherein the puncture device is usable independently therefrom during another portion of the procedure, in order to puncture tissue and to enhance procedural efficiency by facilitating exchange and positioning.

In another broad aspect, embodiments of the present invention comprise a method for puncturing tissue, the method comprising the steps of: (i) accessing a region of tissue within a patient's body by advancing a device into the region of tissue; and (ii) positioning a device at a target tissue site in the region of tissue by tracking a supporting member over the device to support the device to advance the device towards a target tissue site in order to position the device at the target tissue site for puncturing; wherein the steps of accessing and positioning are performed using the same device, wherein the device is usable without the supporting member during the step of accessing and wherein the device is usable with the supporting member during the step of positioning.

In still another broad aspect, embodiments of the present invention comprises a method for puncturing tissue, the method comprising the steps of: (i) accessing a region of tissue within a patient's body using an access device; and (ii) positioning a device at a target tissue site in the region of tissue by tracking a supporting member along with the device along a path defined by the access device to support the device to advance the device towards a target tissue site in order to position the device at the target tissue site for puncturing; wherein the steps of accessing and positioning are performed using separate devices, wherein step of accessing is performed without the supporting member and wherein the device is usable with the supporting member during the step of positioning.

In one broad aspect, embodiments of the present invention comprises a method for puncturing tissue, the method comprising the steps of: advancing a flexible puncture device into a region of tissue; advancing a sheath and a supporting member over the flexible puncture device into the region of tissue; withdrawing the flexible puncture device into the supporting member, positioning the flexible puncture device, the sheath and the supporting member as an assembly at a target tissue site in the region of tissue; tenting with the supporting member, advancing the flexible puncture device to puncture position; puncturing and advancing flexible puncture device; and crossing the sheath and dilator over the flexible puncture device.

In another broad aspect, embodiments of the present invention comprise a method for carrying out a transseptal puncture, comprising the steps of: advancing an RF guidewire into a superior vena cava; advancing a sheath and dilator over the RF guidewire into the superior vena cava; withdrawing the RF guidewire into the dilator, dropping down from the superior vena cava into a heart to find the fossa; tenting with the dilator, advancing the RF guidewire to puncture position; puncturing using the RF guidewire and advancing the RF guidewire; and crossing the sheath and dilator over the RF guidewire.

In still another broad aspect, embodiments of the present invention comprise a method for carrying out a transseptal puncture, the method comprising the steps of: advancing an RF guidewire into a superior vena cava; advancing a sheath and dilator over the RF guidewire into the superior vena cava; inserting a stylet in the dilator until it reaches a stop; withdrawing the RF guidewire into the stylet dropping down from the superior vena cava into a heart to find the fossa; tenting with the dilator, advancing RF wire to puncture position; puncturing and advancing RF wire; crossing the sheath and dilator over the RF wire; and removing the stylet.

In still another broad aspect, embodiments of the present invention comprise a method for carrying out a transseptal puncture, the method comprising: advancing a J-wire into the superior vena cava; advancing a sheath and dilator over the wire into the superior vena cava; removing the J-wire; inserting a needle assembly comprising a stylet and RF guidewire within the dilator at a two finger position; dropping down from the superior vena cava into a heart to find a fossa; tenting with the dilator, advancing needle assembly to puncture position; puncturing and advancing the needle assembly until a stop within the dilator, holding the position and unlocking the RF guidewire; advancing the RF guidewire to anchor, crossing the sheath and dilator over the RF guidewire; and removing the stylet.

In some embodiments of a method of puncturing tissue, the device comprises a flexible energy based puncture device, wherein substantially all of the steps are performed using the flexible energy based puncture device.

In some embodiments of a method of puncturing tissue, the device comprises a flexible RF guidewire and wherein substantially all of the steps are performed using the flexible RF guidewire.

In some embodiments of a method of puncturing tissue, the device comprises a flexible mechanical guidewire having a relatively sharp distal tip wherein substantially all of the steps are performed using the flexible mechanical guidewire.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As an overview of embodiments of the present invention, some embodiments of the system provides a two part assembly comprising a flexible RF component and a rigid support member to enhance the utility of the system. The rigid member such as a reinforcing member is provided separate from and removable from the flexible RF component such as an RF wire and as such can be introduced independently from the flexible RF wire. This provides flexibility in the manner in which the combination of the two components, the RF wire and the reinforcing member can be used. The RF wire can be used independently from the reinforcing member when required—initial advancement of the flexible RF wire in the absence of the reinforcing member removes the need for a separate exchange wire to be used for initial access into the (superior vena cava) SVC. The reinforcing member can then be used selectively—the reinforcing member can be advanced into the SVC to provide adequate force transmission to facilitate the drop down procedure to locate the fossa. If the initial pass at locating the fossa is unsuccessful the two part assembly enables partial removal or withdrawal of the rigid support member to enable the RF wire to be repositioned. The rigid support member may then be re-advanced or re-positioned to provide the adequate stiffness and force transmission to repeat the drop down procedure to locate the fossa and to provide adequate support to facilitate puncture using the RF wire and to facilitate crossing with the RF wire. As such the rigid support member facilitates the transseptal puncture using the RF wire, and functions to additionally facilitate crossing into the left side after the puncture is completed. The reinforcing member may be removed thereafter leaving the flexible RF within the left side of the heart. Thus the flexible RF wire is usable independently from the reinforcing member to facilitate anchoring, facilitate tracking, to minimize left side exchanges to minimize risk of embolisms, and to minimize the risk of trauma. Thus, the reinforcing member can be introduced selectively for a portion of the procedure that requires stiffness and can be removed thereafter (either partially or completely) in order to facilitate the remainder of the procedure. Furthermore, since the reinforcing component is provided separately from the flexible RF wire, the reinforcing component may be re-advanced or reinserted, as desired to complete aspects of the procedure.

In accordance with some embodiments of the present invention, details of the RF wire are disclosed in application number PCT/IB2013/060287 and publication number WO2015019132, which is incorporated herein by reference in its entirety. The details provided herein below include several embodiments of a supporting member usable with a puncture device such as the RF guidewire disclosed in the referenced application.

In some embodiments of the present invention, an assembly is provided for puncturing tissue, where the assembly comprises a substantially flexible puncturing device (that is substantially atraumatic such as an energy based puncturing device) for puncturing tissue via delivery of energy. The assembly additionally comprises a supporting member for supporting the substantially flexible puncturing device such as a rigid needle shaft. In some such examples, the supporting member comprises a reinforcing member (which may form the needle shaft). The supporting member is operable to be selectively usable with the substantially flexible puncturing device and is detachable or removable therefrom. Additionally, the substantially flexible puncturing device is operable independently from the supporting member to puncture tissue. In some such examples, the substantially flexible puncturing device is an energy based device for delivering energy to puncture tissue.

In some such embodiments of the present invention, the substantially flexible energy based puncturing device is selectively usable in co-operation with the substantially rigid supporting member during a portion of the procedure. Additionally the substantially flexible energy based puncturing device is usable independently from the supporting member during another portion of the procedure.

In some such examples, the supporting member is removable from the substantially flexible energy based puncturing device during a portion of the procedure, to enable the substantially flexible energy based puncturing device to be used separately therefrom.

The assembly enables the substantially flexible energy based puncturing device to be usable independently from the supporting member during a portion of the procedure and to be usable in co-operation with during a portion of the procedure. This facilitates exchange by allowing the flexible energy based puncture device to be used for puncturing tissue and as an exchange wire, facilitating exchange and additionally provides the advantage of providing an atraumatic tip for puncturing tissue, as the substantially flexible energy based puncturing is substantially atraumatic. The decoupling of the energy delivery portion of the assembly from the supporting member, additionally enables the supporting member to be removed if the flexible energy based puncturing device is not positioned at the desired target location, enabling the substantially flexible energy based puncturing device to be repositioned to enable the supporting member to be re-advanced over the substantially flexible energy based puncturing device to facilitate positioning of the energy delivery portion of the flexible puncturing device against the desired target tissue location and may additionally reducing procedure complexity and enhance procedural efficiency.

Example 1

Assembly Comprising Puncture Device and Supporting Member

Figure 1B:
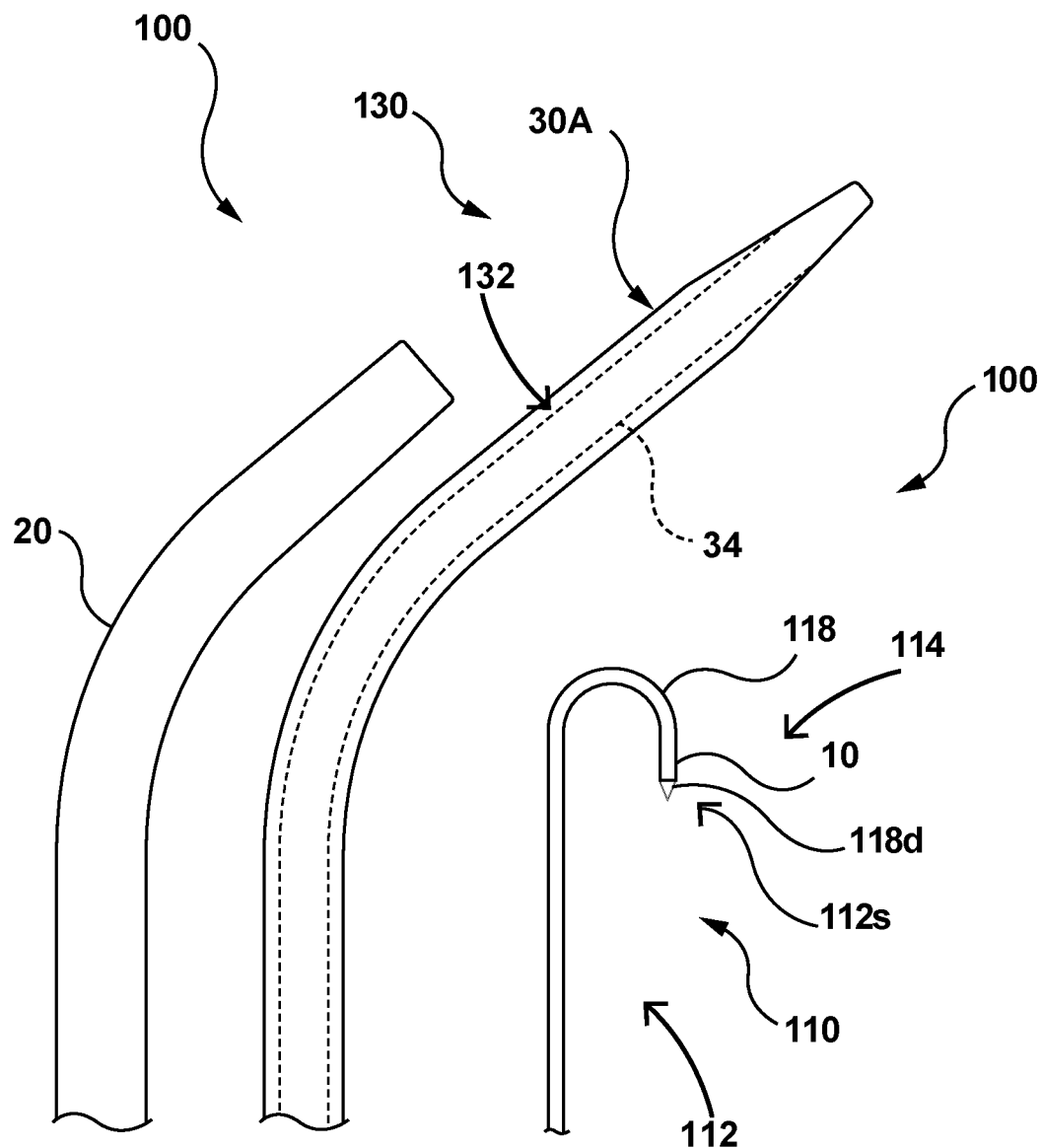

In some embodiments, as shown in FIGS. 1A and 1B, the present invention provides an assembly 100 for puncturing tissue such as for creating a transseptal puncture through a septum of a heart, where the assembly provides a tissue puncture or puncturing device 110, and a separate supporting member 130 that is selectively usable with the tissue puncture device 110 for supporting the puncture device 110. The puncture device 110 is capable of being selectively usable in co-operation with the supporting member 130 during one or more portions or steps of the procedure and the puncture device 110 is usable independently therefrom during another one or more portions or steps of the procedure, in order to puncture tissue. In some such embodiments, providing a separate puncture device 110 and a supporting member 130) for selective therewith additionally enhances procedural efficiency by facilitating exchange and positioning.

With respect again to FIGS. 1A and 1B, in some embodiments, an assembly 100 for puncturing tissue is provided, the assembly 100 comprising a substantially flexible puncture device 112 as discussed further herein below, for puncturing tissue and a supporting member 130 for supporting the substantially flexible puncturing device. The substantially flexible puncture device 112, similar to the embodiment discussed herein above, is capable of being selectively insertable within the supporting member 130 to be selectively usable in co-operation therewith during a portion of the procedure and wherein the substantially flexible puncture device 112 is usable independently therefrom during another portion of the procedure, in order to puncture tissue and to facilitate exchange and positioning. In some such examples, the substantially flexible puncture device 112 comprises an energy delivery device that is operable to deliver energy in order to puncture tissue. In some such examples, as described further in detail herein below, the supporting member 130 comprises a reinforcing member 34.

In one such example, the assembly 100 comprises a needle assembly for puncturing tissue, where the needle assembly comprises the puncture device 110 and the supporting member 130. In some such embodiments of a needle assembly, the puncture device comprises a substantially flexible puncture device 112, as shown in FIGS. 1A and 1B.

In a specific example of the needle assembly, as shown in FIG. 1A, the puncture device 110 comprises a substantially atraumatic distal tip 112d, wherein the puncture device 110 is substantially atraumatic. With reference again to FIG. 1A, in some embodiments, the puncture device 110 comprises an energy based puncture device 114 such as a substantially flexible energy based puncture device 114 that has an energy delivery portion or component 114d at the distal tip thereof for delivering energy in order to puncture tissue. In a specific instance of this example, the puncture device 110 comprises a flexible (radiofrequency) RF guidewire 10 that has a distal electrode tip 10d for delivering radiofrequency energy in order to puncture tissue.

In some instances, the RF guidewire 10 is a flexible wire which is generally electrically insulated save for selected distal regions such as the distal electrode tip 10d.

In a specific example of the needle assembly, as shown in FIG. 1A, the puncture device comprises a mechanical puncture device 118. In some such embodiments, of the needle assembly the mechanical puncture device 118 comprises a relatively sharp distal tip 118d for puncturing tissue.

In some such embodiments of the assembly 100 such as a needle assembly, as shown in FIGS. 1A and 1B, the supporting member comprises a reinforcing member. In some such embodiments, as shown, the supporting member 130 comprises a needle shaft 132 comprising the reinforcing member 34 for supporting the puncture device 110. In some such embodiments, the needle shaft 132 may provide or has properties of a mechanical needle. In a specific example, the reinforcing member [such as a metal hypo-tube] with one or more polymer layers is structured to form a needle shaft 132.

In some embodiments as described herein below, the assembly 100 such as a needle assembly comprises an RF wire and a separate reinforced member. As such, some embodiments of the present invention provided herein below are described with respect to an RF guidewire, but some such embodiment described herein may also be with other puncture devices such as a mechanical puncture device such as a mechanical guidewire. However, an RF guidewire may provide advantages not found in other puncture devices such as a mechanical guidewire Device Example 1

Supporting Member Comprising a Needle Shaft/Reinforced Dilator

In one broad aspect, embodiments of the present invention provide an assembly 100 for puncturing tissue, the assembly 100 comprises a substantially flexible energy based (or energy delivery) puncture device 114 for puncturing tissue via delivery of energy and a supporting member 130 for supporting the substantially flexible energy delivery puncture device 114. The substantially flexible energy delivery puncture device 114 is capable of being selectively insertable within the supporting member 130 to be selectively usable in co-operation therewith during a portion of the procedure and wherein the substantially flexible energy delivery puncture device 114 is usable independently therefrom during another portion of the procedure, in order to facilitate exchange and positioning while providing substantially atraumatic puncture of tissue. In an example the supporting member 130 comprises a reinforcing member 34.

In one such example, with reference now to the embodiment illustrated in FIG. 1A, the assembly 100 comprises a substantially flexible energy delivery puncture device or component 114 that is provided separately from and is operable independently from a supporting member 130. In one such example, the flexible energy delivery puncture device or component 114 (also referred to as a flexible energy based delivery device or a flexible energy delivery puncturing device) comprises a radiofrequency (RF) guidewire 10, and the separate supporting member 130 comprises needle shaft 132 comprising a reinforcing member 34 and one or more polymer layers 38 forming a polymer shaft 39 of the dilator 30A, where the reinforcing member 34 is substantially surrounded by the one or more polymer layers.

Modified Electrode Tip

In the example shown, the RF guidewire 10 comprises an electrode for delivering radiofrequency energy. In one specific example, as shown, the RF guidewire 10 has a distal electrode tip 10d for delivering radiofrequency energy in order to puncture tissue. In some such embodiments, the distal electrode tip 10d is substantially atraumatic to reduce the pressure exerted on the tissue. In one such example, the distal electrode tip of the RF guidewire 10 comprises a substantially dome-shaped electrode tip that is substantially atraumatic to reduce the pressure exerted on the tissue.

In some such examples, with reference to FIG. 1A, the RF guidewire 10 may comprise a cylinder as shown by reference number 10c with a hemispherical electrode tip 10d which in some examples may form a cap that is formed distal to and adjacent to the cylinder 10c. In other words, the electrode tip 10d may be defined by a dome on top of the cylinder 10c, such as a substantially full round dome. In some such examples, the outer diameter of the dome may substantially match the outer diameter of the cylinder 10c. This may help provide a substantially atraumatic distal interface with the tissue to minimize risk of trauma and/or injury at the desired target tissue site. In some such embodiments, the dome shaped distal electrode tip 10d of the RF guidewire 10 may reduce the amount of pressure that is exerted by the distal tip on the tissue to make the tip more atraumatic, so a force exerted by the distal tip is spread over a larger area. In some such examples, the RF guidewire 10 is provided as a 0.035" wire.

Figure 1C:
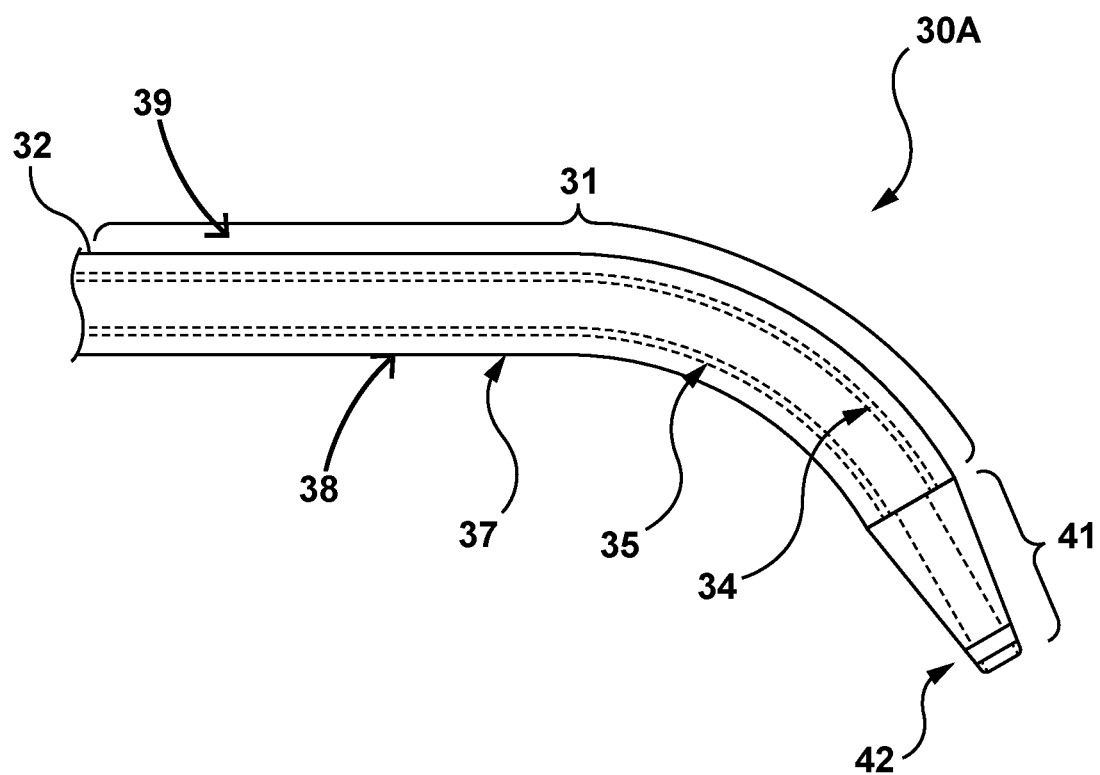

More specifically, with reference to FIGS. 1A and 1C, the assembly additionally comprises a sheath 10 and a supporting member comprising a reinforced dilator such as dilator 30A that are usable with the flexible RF wire, where the dilator 30A comprises the reinforcing member 34 and one or more polymer layers 38 defining a polymer shaft 39 of dilator 30A, where the reinforcing member 34 is substantially surrounded by the one or more polymer layers 38.

In some such embodiments of the present invention, an assembly 100 is provided for puncturing tissue, where the supporting member 130 comprises a needle shaft 132 where the needle shaft 132 comprises the reinforcing member 34 and one or more polymer layers 38, where the reinforcing member 34 is substantially surrounded by the one or more polymer layers 38. In some such embodiments, the needle shaft 132 is provided within the dilator 30A. As such, in some embodiments, the supporting member comprises a needle shaft 132 that is provided as a part of or defined by the dilator 30A, wherein the needle shaft 132 is embedded in or surrounded by one or more polymer layers 38 of the dilator 130.

Details of the reinforcing member 34 are shown in FIG. 1C. More specifically, FIG. 1C illustrates a supporting member 130 that comprises a reinforced dilator 30A having the needle shaft 132, where the supporting member 130 is provided separately from the substantially flexible tissue puncturing device or member 112, such as an energy based tissue puncturing device 114 such as an RF guidewire 10. In one example, the needle shaft 132 is provided as a part of or in other words is defined by the dilator 30A. In some such examples, needle shaft 132 (and thus the dilator 30A defining the supporting member 130) is provided as a non-puncturing component for supporting the tissue puncturing device or member. In some such examples, the dilator 30A comprising the needle shaft 132 comprises a proximal portion 31 that terminates at a distal tip 41. In some such embodiments, the reinforcing member 34 provides sufficient rigidity that is substantially similar to that of a rigid needle.

In some such examples, a dilator shaft 32 extends along the proximal portion 31 and comprises the reinforcing member 34. In the particular example shown, the reinforcing member 34 is substantially surrounded by the one or more polymer layers 38. In some such examples the reinforcing member 34 is embedded within the one or more polymer layers 38 which comprise an inner polymer layer and an outer polymer layer. In some such examples, the inner and outer polymer layers comprise inner and outer tubular members 35, 37 of the dilator shaft 32. In some such examples, substantially surrounded may be taken to mean that the reinforcing member 34 is substantially surrounded on its outside or its exterior by the one or more polymer layers 38 that form a polymer shaft 39 (forming the dilator shaft 32) around the reinforcing member 34. In some embodiments, the dilator 30A may additionally include a radiopaque marker 42 at the distal tip 41. In one example, the reinforcing member 34 comprises a hypo-tube such as a metal hypotube. In one such example, the reinforcing member 34 comprises a stainless steel hypotube and the inner and outer tubular members 35, 37 comprise HDPE.

Hypo-Tube Defines an Inner Lumen of the Supporting Member

In one such example, the reinforcing member 34, such as the stainless steel hypo-tube, extends longitudinally within the one or more polymer layers, for example, within the inner and outer tubular members 35, 37, as shown in FIG. 1C. As such, the reinforcing member 34 [for example a hypotube] defines an inner lumen of the supporting member 130.

Hypo-Tube Located Between One or More Polymer Layers

In one example, the supporting member 130, with reference again to FIG. 1C, the one or more polymer layers 38 comprise an inner polymer layer and an outer polymer layer, which in some examples may comprise inner and outer tubular members 35, 37. In a specific instance, the reinforcing member 34 is substantially surrounded by the one or more polymer layers 38 along its exterior, as noted above. In other examples, the reinforcing member 34 is substantially surrounded by the one or more polymer layers 38 such that the reinforcing member 34 is located between the inner polymer layer and an inner polymer layer, for example, as defined by the inner and outer tubular members 35, 37 shown in FIG. 1D (in some examples, the hypo-tube is located between or sandwiched between two layers of polymer. In other words, the reinforcing member 34 is substantially surrounded by and embedded within both the inner and outer polymer layers. In other words the reinforcing member 34 is sandwiched or located between the inner and outer polymer layers 38 and thus the polymer shaft 39 that forms the dilator shaft 32. In some such examples, the inner and outer tubular members 35, 37 comprise high density polyethylene (HDPE).

In some embodiments of the transseptal assembly 100, the sheath 10 comprises a standard transseptal sheath, the needle shaft 132 (provided as a part of or defined by the dilator 30A) comprising a reinforcing member 34 as described herein above and the RF guidewire or RF wire is provided as a 0.035" wire. In some such examples, the RF wire comprises a J-tip wire or in alternate examples the RF wire comprises a pigtail wire.

Hypo-Tube Secured within an Inner Lumen of the Dilator

In some such embodiments of the present invention, the reinforcing member 34 comprises a distal end 34D and a proximal end 34P, where the reinforcing member 34 extends within an inner lumen of the dilator 30A, as shown in FIG. 1C. In some such embodiments, the assembly 100 provides a substantially gapless interface at the junction between the reinforcing member at the distal and proximal ends and the one or more polymer layers. In some such examples, the reinforcing member 34 is secured within the one or more polymer layers 38 forming the polymer shaft 39 of the dilator 30A. In one such example, with reference now to FIGS. 7A-7C, the reinforcing member 34 is substantially affixed at its distal and proximal ends (in other words the reinforcing member distal and the reinforcing member proximal end) to the one or more polymer layers 38 of the dilator 30A to provide a substantially gapless interface at the junction between the reinforcing member 34 at the distal and proximal ends and the one or more polymer layers 38 reinforcing member. The drawings show the interface at the distal end of the reinforcing member 34. A similar interface is provided at a proximal end of the reinforcing member 34. In some such embodiments of the present invention, the reinforcing member 34 is substantially scaled at its distal and proximal ends (in other words at the reinforcing member distal end and the reinforcing member proximal end) to the one or more polymer layers 38 of the dilator 30A. In some such embodiments, by substantially eliminate the gap between the reinforcing member 34 and the polymer shaft 39 of the dilator 30A, this may prevent blood or other liquid from getting between the reinforcing member 34 and the polymer shaft 39.

Force Transmission and/or Torque Transmission

Supporting Member Providing Force Transmission/Torque

In some such embodiments of the present invention, the supporting member 130 provides sufficient stiffness to the puncturing device such as the RF wire to enable sufficient force transmission to enable force to be transmitted to a distal end of the assembly 100.

In some such embodiments, the supporting member 130 provides sufficient stiffness to the puncturing device to enable torque to be transmitted to a distal end of the assembly.

Reinforcing Member Providing Force Transmission/Torque

In some such examples, the reinforcing member 34 provides sufficient stiffness to the supporting member 130 to enable sufficient force transmission to enable force to be transmitted to a distal end of the assembly 100. More specifically, the reinforcing member 34 provides sufficient stiffness to the assembly 100 such that the substantially flexible puncturing device 112 (such as a substantially flexible energy based puncture device 114 such as an RF wire 10) together with the supporting member 130 is capable of sufficient force transmission to enable force to be transmitted to a distal end of the assembly 100 (and thus allows force to be transmitted to a distal end of the substantially flexible puncturing device 112).

As such, the reinforcing member 34 is capable of imparting force transmission capabilities to the substantially flexible RF wire 10, which when used together with the supporting member 130 is capable of force transmission to enable force to be transmitted to a distal end of the assembly 100, for example for engaging tissue at a target tissue site. As such the reinforcing member 34 functions as a force transmitting portion of the assembly 100.

In some such examples, the assembly 100, further comprises a sheath 20, as shown in FIG. 1A, where the sheath 20 is usable with the supporting member 130, to provide stiffness to the assembly 100 to facilitate force to be transmitted to a distal end of the assembly 100.

In some such embodiments of the present invention, the reinforcing member 34 provides sufficient stiffness to enable torque to be transmitted to a distal end of the assembly 100. As such, the reinforcing member 34 provides sufficient stiffness to the assembly, wherein the substantially flexible puncturing device 112 such as a substantially flexible energy based puncturing device 114 together with supporting member 130 provides sufficient stiffness to the assembly 100 to enable torque to be transmitted to a distal end of the assembly 100 (and thus allows torque to be transmitted to a distal end of the substantially flexible puncturing device 112).

Some such embodiments of the present invention facilitate transseptal puncture, where the reinforcing member 34 provides sufficient stiffness to the assembly 100 to enable sufficient force transmission for engaging a desired tissue site (such as the septum of the heart). In some such example, the supporting member 130 provides the substantially flexible puncture device 112 with force transmission capabilities where the substantially flexible puncture device 112 is capable of force transmission when in use with the supporting member 130.

In some such embodiments, the assembly 100 further comprises a sheath 20, as shown in FIG. 1A, where the sheath 20 is usable with the supporting member 130, to provide stiffness to the assembly 100 to enable torque to be transmitted to a distal end of the assembly 100.

In some such examples, the sheath 20 may be coupled to the dilator 30A which enables force and/or torque transmission using one or more of the components [i.e., the sheath 20 or the dilator 30A.]. In other words, the user may not have to manipulate the sheath 20 and the dilator 30A (the user may just manipulate the sheath 20 or the dilator 30A) and the RF guidewire 10 follows the guidance and/or direction of the sheath 20 and/or the dilator 30A. In some such examples, the sheath 20 has some contribution to the overall torque. In some such embodiments, torqueing the sheath 20 and/or the dilator 30A enables the reinforcing member 34 to be torqued therewith.

Stiffness of the Reinforcing Member

In some embodiments of the present invention, the force transmitting portion of the assembly 100 has a force transmitting portion flexural rigidity of at least about 0.0085 $Nm^2$, for example about 0.0115 $Nm^2$. In some embodiments of the present invention, the force transmitting portion of the assembly is the supporting member 130 that has a stiffness or rigidity with a flexural rigidity value of at least about 0.0115 Nm² to enable sufficient force transmission to enable force to be transmitted to a distal end of the assembly 100. In some such examples, the supporting member has a flexural rigidity of about 0.0085 Nm² to about 0.0145 Nm². In one such example, the supporting member 130 is the reinforced dilator 30A that has a flexural rigidity of at least about 0.0085 Nm², for example about 0.0115 Nm². In a specific example, the reinforced dilator 30A has a flexural rigidity about 0.0085 Nm² to about 0.0145 Nm². In one such example, the reinforced dilator 30A is the reinforced dilator 30A as provided in Example 1, for example as provided with respect to FIGS. 2A-2G.

In some such examples, the supporting member 130 functions to impart rigidity or stiffness to the assembly 100 including the puncture device such as a substantially flexible puncture device, to provide force transmission capabilities to the assembly including the puncture device such as a substantially flexible puncture device.

In some examples, the flexural rigidity values provided for the supporting member 130 are also usable for Examples 2 and 3 provided herein with respect to FIGS. 4A-4G, and FIGS. 6A-6H.

Examples 2 and 3

In some embodiments of the present invention, the force transmitting portion of the assembly is the supporting member 130 that is the reinforcing member that comprises the stylet. The stylet has a stiffness or rigidity with a flexural rigidity value of at least about 0.008 Nm², for example about 0.015 Nm² to enable sufficient force transmission to enable force to be transmitted to a distal end of the assembly 100. In some such examples, the supporting member has a flexural rigidity of about 0.008 Nm² to about 0.024 Nm².

Stiffness of the Puncture Device

In some embodiments of the present invention, a distal portion of the puncture device such as a substantially flexible puncture device has a distal portion or distal region flexural rigidity. In some such examples, a substantially flexible RF guidewire 10 is provided, where the substantially flexible RF guidewire 10 has a distal portion [including along the distal electrode tip 10d] where the RF guidewire 10 has a distal portion stiffness defined by a flexural rigidity of at least about $3.57 \times 10^{-6}$ Nm², for example about $4.76 \times 10^{-6}$ Nm². In some embodiments of the present invention, RF guidewire 10 has a distal portion stiffness or rigidity with a flexural rigidity of between about $3.57 \times 10^{-6}$ Nm² to about $5.95 \times 10^{-6}$ Nm².

In some such examples, the distal region of the RF guidewire 10 is tapered down from a proximal region of the RF guidewire 10, over about 12 cm-15 cm. In other words, the distal portion of the RF guidewire 10 has a length of between about 12 cm to about 15 cm. In some such examples, the distal portion of the RF guidewire 10 is the thinnest point of the RF guidewire 10.

In some such embodiments, the substantially flexible RF guidewire 10 has a proximal portion with a proximal portion flexural rigidity of less than about 0.00179 Nm², for example about 0.00143 Nm². In some embodiments of the present invention, RF guidewire 10 has a proximal portion stiffness or rigidity with a flexural rigidity of between about 0.00107 Nm² to about 0.00179 Nm².

In some embodiments of the present invention, where the substantially flexible puncture device comprises an RF guidewire 10 has a flexural rigidity of between about $2.0 \times 10^{-6}$ to about $1.4 \times 10^{-3}$ Nm². In some such examples, the RF guidewire 10 has a wire diameter that is between about 0.127 mm to about 0.635 mm.

Supporting Member/Reinforcing Member Shape-Ability

More specifically, the reinforcing member 34 is shapeable to enable the supporting member 130 (for example comprising a needle shaft 132 as provided as a part of or defined by a reinforced dilator 30A) to be removed from the substantially flexible energy delivery puncturing device 110 (such as the RF wire 10) to enable a curve of the supporting member 130 be re-shaped to be reinserted therewith, in order to optimize the position of the assembly 100 against a target tissue site, such as the fossa of the septum of the heart.

In some embodiments of the present invention, the supporting member 130 is shapeable to enable it to be removed from the puncture device (such as substantially flexible puncture device 114 such as an RF guidewire 10) to enable a curve of the supporting member 130 be re-shaped to be reinserted therewith, in order to optimize the position of the assembly 100 against a target tissue site. In some such examples, the reinforcing member 34 additionally provides shapeability, and enables the reinforcing member 34 and thus the supporting member 130 to be shapeable. In some such embodiments, where the reinforcing member 34 is shapeable enable the supporting member 130 (that includes the reinforcing member 34) to be removed from the substantially flexible puncture device (such as an RF guidewire) to enable a curve of the supporting member be re-shaped to be reinserted therewith, in order to optimize the position of the assembly 100 against a target tissue site, such as the septum of the heart.

In some such embodiments, the supporting member 130 comprises a reinforcing member 34 that is provided within the reinforced dilator 30A (such as within a needle shaft 132 of the reinforced dilator 30A), and as such imparts shapeability to the dilator 30A. In other examples, the supporting member 130 comprises a stylet 60 that is provided separately from the dilator 30A (as described in embodiments described further herein below and imparts shapeability to the assembly 100. In other words the stylet 60 functions to impart a desired curvature and stiffness to the assembly 100 when in use with the assembly 100. The stylet 60 is removable from the assembly and can be re-shaped and re-inserted into the assembly 100 to provide a desired curvature to the assembly 100.

Coupling Between Dilator and Sheath

Locking Feature for Example 1

In some embodiments of the present invention, with reference now to FIG. 1C, and assembly 100 is provided that comprises a sheath 20 as shown in FIG. 1A for use a sheath for use with the reinforced dilator 30a for use therewith during a portion of the procedure. In some such examples, the assembly 100 comprises a locking mechanism to enable axial and rotational coupling of the dilator 30A with the sheath 20 for a portion of the procedure. In some embodiments of the present invention, the locking mechanism enables co-operative engagement between the sheath 20 and dilator 30A to provide rotational and axial coupling. This may help minimize the risk of rotational misalignment between the sheath 20 and dilator 30A and thus may reduce the risk of confusion resulting from the misalignment.

Referring now to FIG. 1E, the supporting member 130 comprising a needle shaft 132 (as provided as part of or defined by) dilator 30A comprises a dilator hub 51 that is operable to be coupled to the sheath hub 21 for a portion of the procedure. In one example, as illustrated in FIG. 1F, a locking mechanism is provided where the dilator hub 51 comprises one or more keys 52 for co-operatively engaging with corresponding features (such as key receiving features) on the sheath hub 21 that enable axial and rotational locking with the sheath 20. As such in some embodiments of the present invention a locking mechanism is provided to enable axial and rotational coupling of the dilator with the sheath for a portion of the procedure. In some examples, a steerable sheath is provided, where the steerable sheath 20 may be an 8 Fr steerable sheath. Alternatively, an 8.5 Fr steerable sheath 20 may be provided. In some such examples, the steerable sheath 20 may be provided with different curvatures. In a specific example, steerable sheaths 20 may be provided in different curvatures, specifically at angles of: 37, 45, 55, 90, or 135 degrees. In a specific instance of this example, the sheath tubing comprises an inner PTFE liner, a braid and a Pebax outer jacket. In some such embodiments, a supporting member 130 comprising a needle shaft 132 (for example, provided as a part of or defined by) an 8 Fr dilator 30A is provided that is compatible with an 8 Fr Sheath. Alternatively, supporting member 130 comprising the needle shaft 132 may be provided as a part of, or defined by an 8.5 Fr dilator 30A may be provided that is compatible with an 8 Fr steerable sheath 20. The supporting member 130 comprising the needle shaft 132 (for example as provided as a part of or defined by dilator 30A) may be provided with a 50 degree or 86 degree curvature. In some examples, materials may include HDPE and a metal hypotube that forms the reinforcing member 34. In some such examples, the RF wire comprises a 0.035" OD wire and may be a J-tip wire or a pigtail wire. In a specific instance of this example, the wire may comprise a stainless steel core with a PTFE coating.

Radiopaque Markers

In some embodiments, as shown in FIGS. 1C and 1D, the supporting member 130 comprises one or more radiopaque markers such as a supporting member radiopaque marker 42. In some such examples as above, the assembly 100 provides a supporting member 130 (for example comprising a needle shaft 132 as provided as a part of or defined by a reinforced dilator 30A), comprises a radiopaque marker 42, such as at the distal tip of the supporting member 130. In some such examples, the supporting member 130 comprises a radiopaque marker 42 embedded within the polymer of the distal tip thereof, as shown.

Figure 7A:
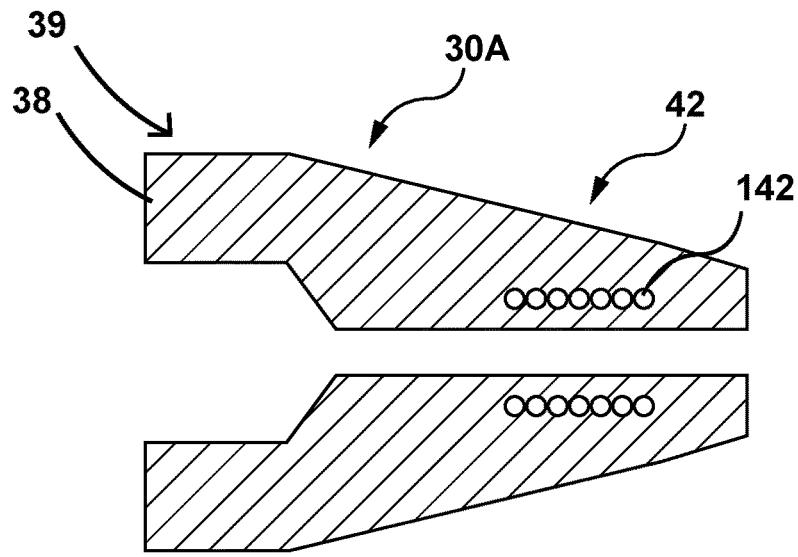
FIGS. 7A-7C illustrate a dilator, in accordance with additional alternate embodiments of the present invention.
Figure 7B:
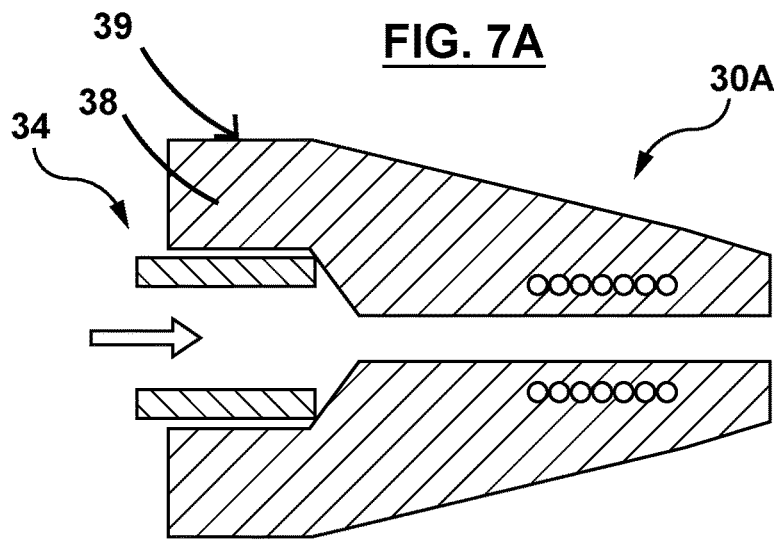
Figure 7C:
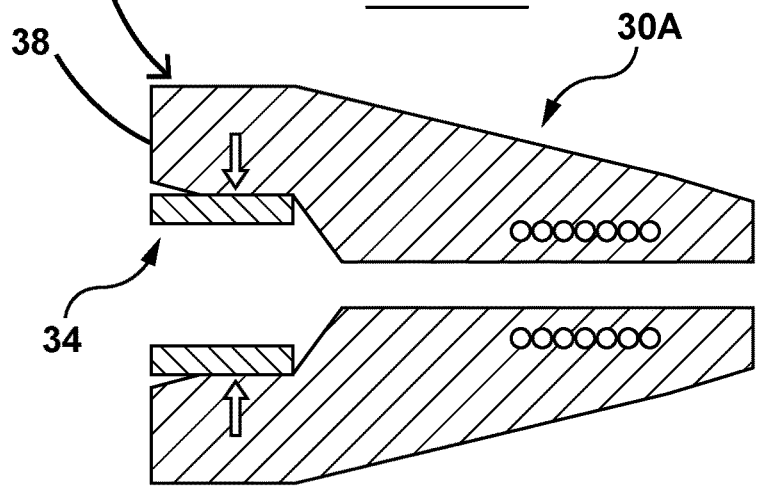

In a specific example, as shown in FIGS. 7A, 7B and 7C, the radiopaque marker 42 comprises a radiopaque coil 142 embedded within the polymer of the supporting member 130 (for example comprising a needle shaft 132 as provided as a part of or defined by a reinforced dilator 30A) such as within the one or more polymer layers 38 (forming the polymer shaft 39 which in turn forms the dilator shaft 32), for example, at a distal tip thereof (of the supporting member 130). In a more specific example, the radiopaque coil 142 is embedded within the one or more polymer layers such that the one or more polymer layers extend distally beyond the radiopaque coil 42.

Alignment Using Radiopaque Markers

Figure 3A:
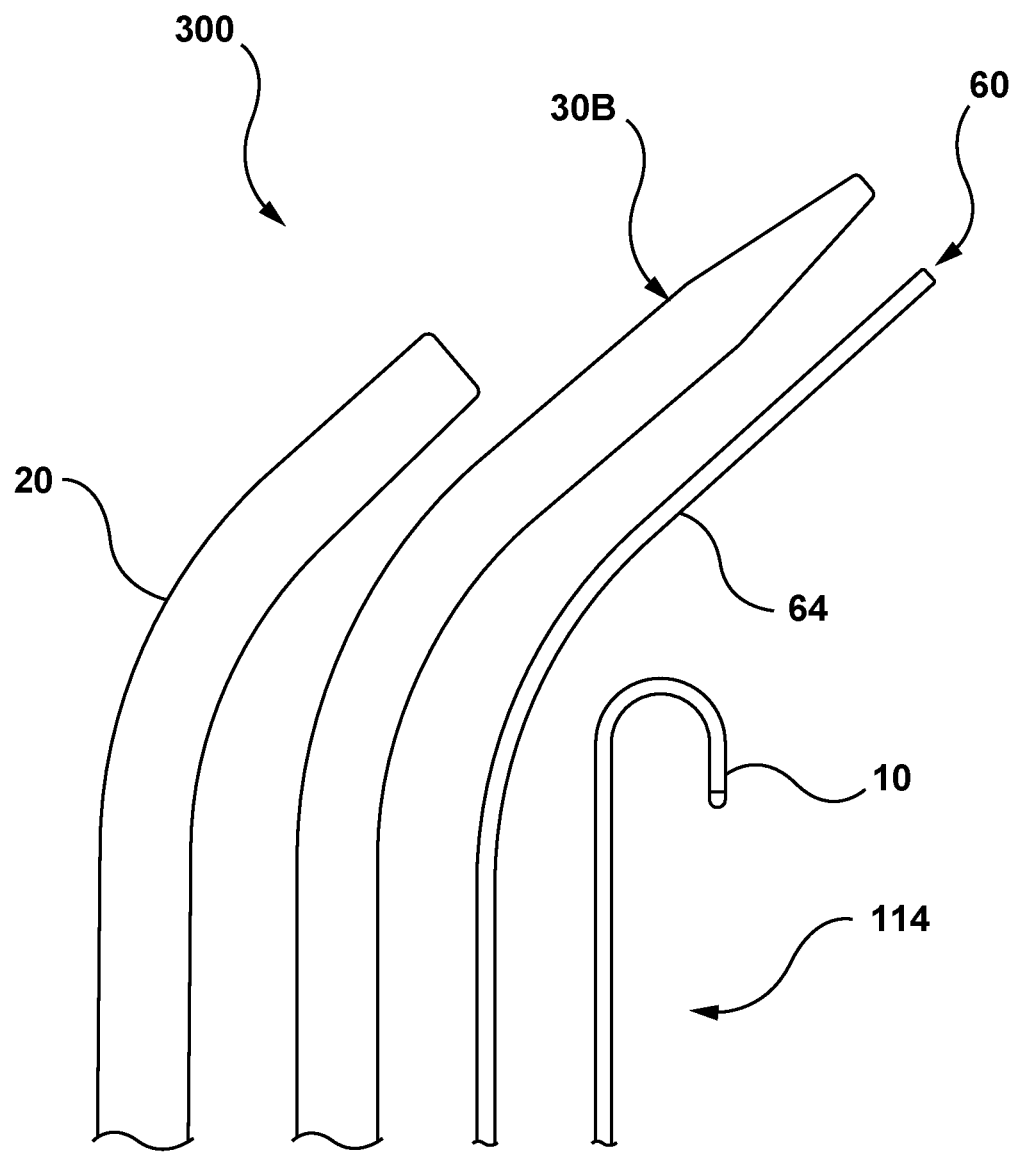
FIG. 3A is an illustration of a transseptal assembly in accordance with an alternate embodiment of the present invention.
Figure 3B:
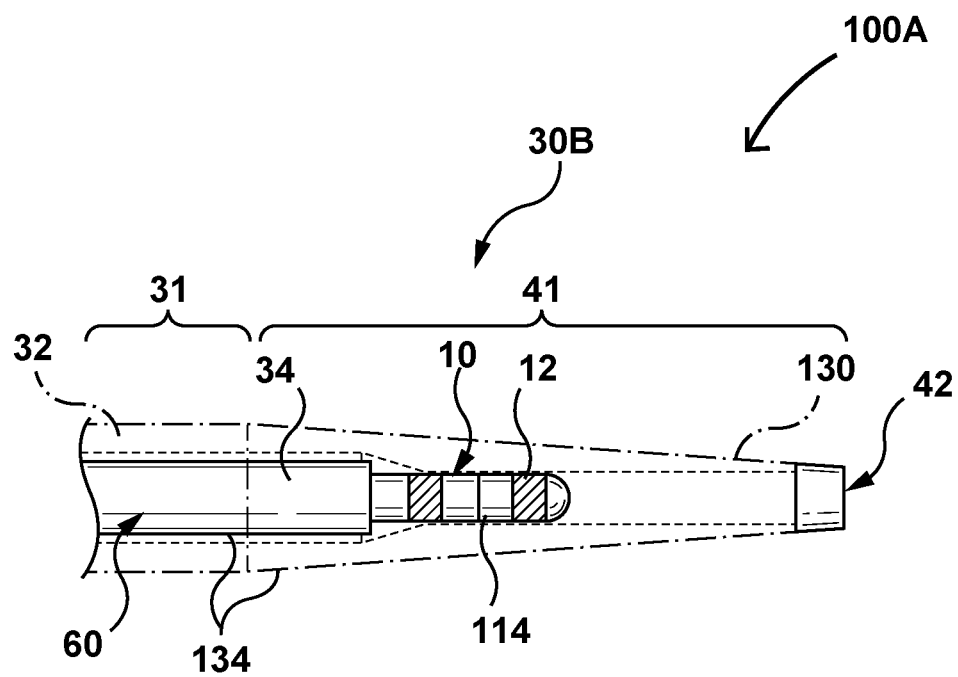
FIG. 3B shows an assembly comprising a dilator, a stylet defining a reinforcing member, and an RF wire, in a drop down position, in accordance with an embodiment of the present invention.
Figure 3C:
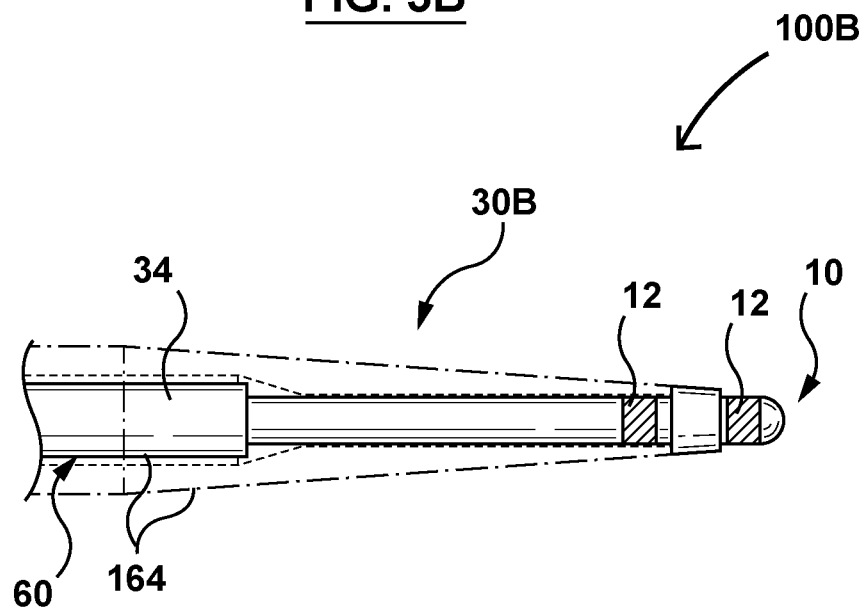
FIG. 3C shows an assembly comprising a dilator, a stylet defining a reinforcing member, and an RF wire, in an arcing position, in accordance with an embodiment of the present invention.

In some embodiments of the present invention, a substantially flexible energy based puncturing device 114 is provided (such as an RF guidewire) that comprises one or more device side radiopaque markers (or in other words one or more device radiopaque markers) at a distal end of thereof, for example, as shown in FIGS. 3B and 3C. In some such embodiments, as noted above, the supporting member 130 also comprises a supporting member radiopaque marker at the distal end of the supporting member 130 (as shown in FIGS. 1C and 1D). In some such examples, similar to the embodiments shown in FIGS. 3B and 3C, the one or more device radiopaque markers 12 are configured to co-operate with the supporting member radiopaque marker 42 to indicate the relative position of the substantially flexible energy based puncturing device 114 (such as an RF guidewire 10). The embodiments, shown in FIGS. 3B and 3C illustrate a dilator 30B that is provided separately from a stylet 64. However, in alternative embodiments as described currently the stylet 64 may be a reinforcing member 34 that is provided within a dilator 30A.

In some such embodiments, the assembly 100 comprises an initial configuration 100A, where the substantially flexible energy based puncturing device 114 (such as an RF guidewire 10) is positionable within the supporting member 130 such that the one or more device radiopaque markers 12 are not in alignment with the supporting member 130 radiopaque marker 42, as shown in FIG. 3A. In some such examples, multiple radiopaque markers may be visible under imaging, including the one or more device radiopaque markers 12 and the supporting member radiopaque marker 42.

In some such embodiments, the assembly 100 comprises a first configuration 100B, as shown in FIG. 3B where the substantially flexible energy based puncturing device 114 (such as an RF guidewire 10) is positionable within the supporting member 130 such that the one or more device radiopaque markers 12 are in alignment with the supporting member 130 radiopaque marker 42, as shown in FIG. 3B. In some such examples, a single radiopaque marker may be visible under imaging [including the one or more device radiopaque markers 12 and the supporting member radiopaque marker 42 that may be arranged in close proximity to one another].

The assembly 100 additionally has a second configuration 100B, where the substantially flexible energy based puncturing device 114 (such as an RF guidewire 10) is positionable/advanceable within the supporting member 130 such that the one or more device radiopaque markers 12 are substantially not in alignment or misaligned with the supporting member radiopaque marker 42. In some such examples, the misalignment of the one or more device radiopaque markers 12 with the supporting member radiopaque marker 42 indicates positioning of an energy delivery portion 114*d* of the flexible energy based puncturing device 114 (such as an RF electrode tip 10*d* of an RF guidewire 10) beyond the supporting member (for example distal to the distal tip or end of the supporting member 130) for positioning against a target tissue site for puncture of tissue. In some such examples, similar to FIG. 3A, multiple radiopaque markers may be visible under imaging [including the one or more device radiopaque markers 12 and the supporting member radiopaque marker 42, where the one or more device radiopaque markers 12 are positioned distally to the supporting member radiopaque marker 42, indicating that the distal electrode tip lid is positioned against a target tissue site (such as the septum of the heart) for puncturing the tissue.

In some such examples, the sheath 20, and dilator 30A as well as the reinforcing member 34 are all radiopaque, and have radiopaque properties to enable them to visible under imaging. In some such examples, one or more of the sheath 20, dilator 30A, and reinforcing member 34, such as a metal hypo-tube comprise radiopaque materials in addition to radiopaque markers [42]. The reinforcing member 34 such as a metal shaft or hypotube is also radiopaque. In some such embodiments, polymers forming the sheath 20 and/or the dilator 30A may comprise polymer radiopaque filler such as barium sulfate 20% so there is contrast with the one or more markers [12, 42] at the distal tip. In other words this may provide visibility under imaging and may additionally provide contrast with the one or more markers [42, 12] which may allow the user to see the dilator 30A in comparison to the RF guidewire 10 under imaging, to see whether the RF guidewire 10 is positioned in or outside the dilator 30A [i.e., whether the distal segment of the RF guidewire 10 is distal to the dilator 30A.

Blunt Dilator Tip [Example 1]

In some embodiments of the present invention, the supporting member 130 comprises a substantially blunt distal tip or edge 143, as shown in FIG. 1A, in order to provide a substantially atraumatic distal tip 143, while providing the advantages of a substantially rigid or stiff supporting member 130 (such as by providing the reinforcing member 34) therein. In some such embodiments, as noted above, a reinforced dilator 30A is provided, with reference again to FIG. 1A. The dilator 30A in some instances comprises a substantially blunt distal tip or edge 144 in order to provide a substantially atraumatic distal tip 144. In some such embodiments, the reinforced dilator 30A comprises a substantially thick distal wall along the distal tip 144 where the distal tip 144 is defined by a substantially rounded distal tip edge. In some such embodiments, the dilator 30A provides advantages of a dilator by providing a substantially atraumatic distal tip and additionally a tapered profile at the distal tip to provide ease of trackability and crossing while providing advantages associated with providing a substantially rigid body by providing a substantially rigid component (such as a reinforcing member 34 therein) in addition to enabling use of an RF guidewire 10 for one or more of positioning, tracking devices, puncturing and anchoring.

In one such embodiment, an overall method/workflow is provided that illustrates a method of carrying out a transseptal puncture procedure using an assembly 100, as described herein above. The method disclosed herein provides one or more advantages associated with an assembly comprising an energy delivery component that is provided separately from the rigid component. Details of the method are provided herein below.

Method

Method [Example 1]

Using the Same Device for Initial Track Up/Access and Positioning

Figure 2A:
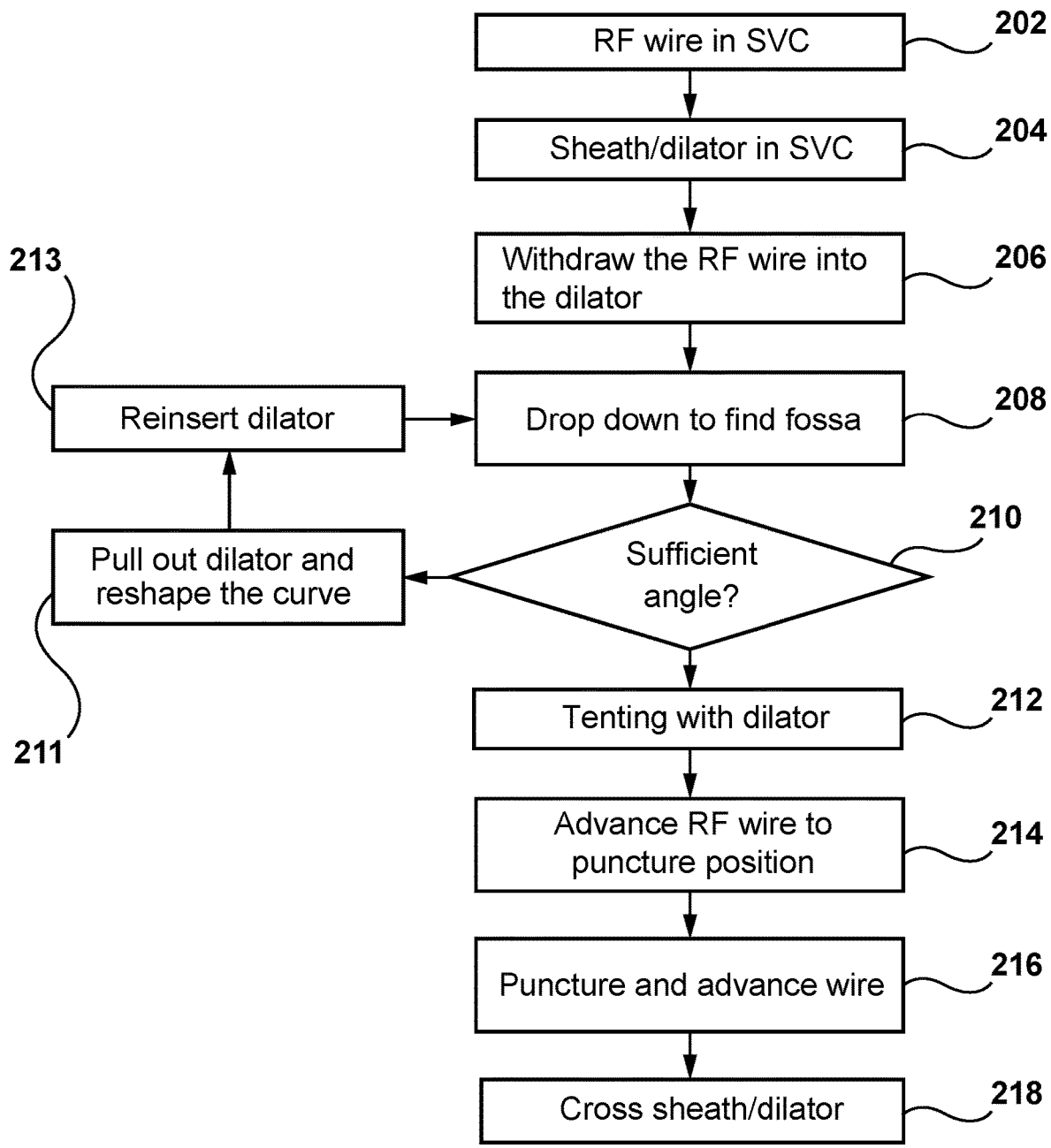
FIG. 2A is an illustration of a flow diagram showing a method of performing a transseptal procedure, in accordance with an embodiment of the present invention.
Figure 2B:
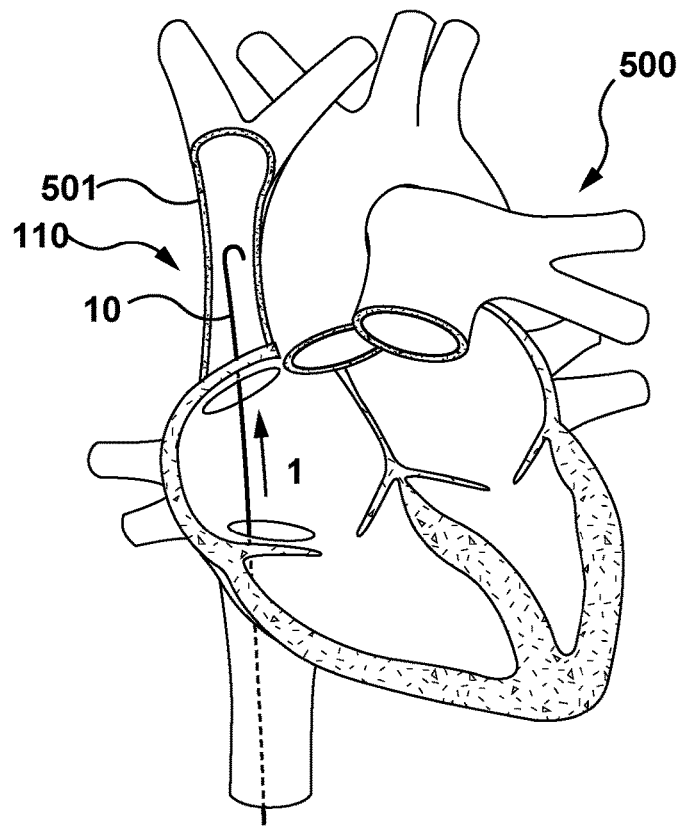

In some embodiments of the present invention, with reference now to FIGS. 2A-2G, a method is disclosed for puncturing tissue. The method comprises the step of: [1] accessing a region of tissue within a patient's body by advancing a device (such as a puncture device 110 such as an RF guidewire 10) into the region of tissue, as shown in FIG. 2B. In some such examples the method of puncturing a region of tissue comprises a method of carrying out a transseptal puncture where the step of accessing the region of tissue comprises advancing the device (such as the puncture device 110) into the superior vena cava (SVC) 501 adjacent a heart 500 of the patient.

Figure 2C:
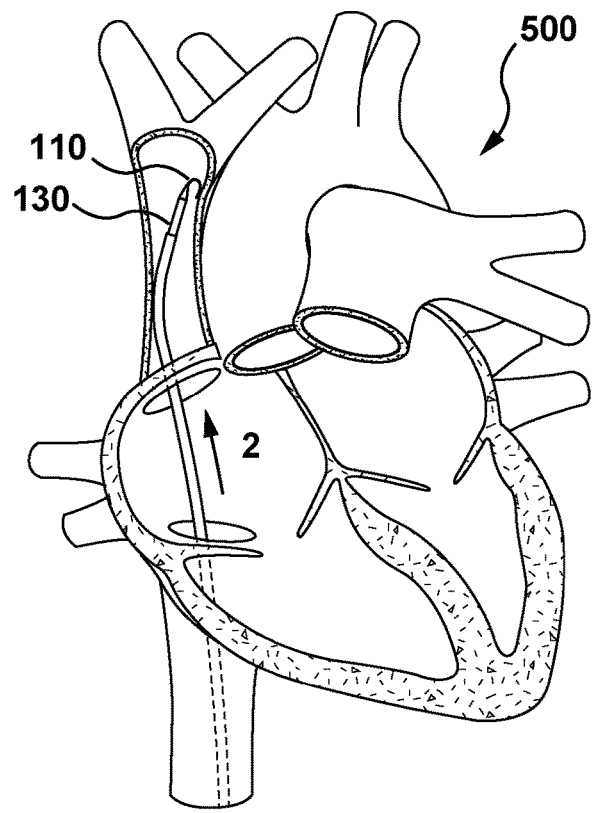

In some embodiments of the present invention, the method for puncturing tissue additionally comprises the step of: [3] positioning a device at a target tissue site in the region of tissue, as shown in FIG. 2D, by for example: [2] first tracking a supporting member 130 (such as reinforced dilator 30A) over the puncture device 110 to support the device (such as puncture device 110) as shown in FIG. 2C, to [3] enable advancement of the device (such as a puncture device 110) towards a target tissue site in order to position the device at the target tissue site for puncturing, as shown in FIG. 2D.

In some such examples, the step of positioning the puncture device 110 at the target tissue site comprises performing [3] a drop down from the superior vena cava (SVC) into the heart 500 of the patient to locate a fossa ovalis (or in other words fossa) 504 along a septum 502 of the heart 500, by first for example (2) tracking or advancing a supporting member 130 (such as a dilator 30A) over the device (such as a puncture device 10) into the SVC to (3) facilitate the drop down to position the puncture device 110 at the fossa 504.

In some such examples, as shown in FIGS. 2B-2D, the steps of accessing [1], as shown in FIG. 2B and positioning [3], as shown in FIG. 2D, are performed using the same device such as a puncture device 110, wherein the puncture device 110 is usable without the supporting member 130 during the step of accessing [1] and wherein the device is usable with the supporting member 130 during the step of positioning [3].

Using a Puncture Device for Initial Access and Positioning

In some such embodiments of the present invention, as shown in FIGS. 2B-2D, the steps of accessing and positioning are performed using a puncture device 110.

Using the Same Device for Initial Access, Positioning and Puncturing

In some such embodiments of the present invention, as shown in FIG. 2E, the method additionally comprises: [4] a step of puncturing through the target tissue site using a device (such as the puncture device 110) after the step of positioning [3] as shown in FIG. 2D. The supporting member 130 supports the device (such as puncture device 110) during puncturing [4] where the steps of accessing [1], positioning [3] and puncturing [4] are performed using the same device.

In some embodiments of the present invention, the step [4] of puncturing through the target tissue site comprises the step [4] of puncturing through the fossa 504 to gain access to a left side of the heart 500. This enables one or more devices of the assembly 100, such as the supporting member 130 (such as dilator 30A) and sheath 20 of the assembly 100 to be tracked over the RF guidewire 10 into the left side of the heart.

Using a Puncture Device for Initial Access, Positioning and Puncturing

In some such examples, as shown in FIGS. 2B-2E, the steps of accessing, positioning, and puncturing are performed using a puncture device 110.

Using the Same Device for Initial Access, Positioning and Puncturing and Anchoring In accordance with an embodiment of the present invention, the method additionally comprises a step of anchoring, as shown in FIG. 2E, where the step of anchoring is performed using a device (such as the puncture device 110) after the step of puncturing [4] through the target tissue site, to maintain access through the target tissue site to the other side of the target tissue site, to allow one or more additional device [such as sheath 20 and the supporting member 130 comprising the dilator 30A] to be tracked over the device (such as the puncture device 110) to the other side of the target tissue site, as shown in FIG. 2F, where the steps of accessing, positioning, puncturing and anchoring are performed using the same device. The puncture device 110 such as the RF guidewire 10 may be left to maintain access to the left side of the heart, as shown in FIG. 2G. The supporting member 130 for example comprising the dilator 30A may be removed or retracted to allow anchoring using the RF guidewire 10. The RF guidewire 10 functions as a rail to guide one more devices to the left side of the heart. In some such examples, the RF guidewire 10 provides a substantially stiff rail to guide the one or more devices to left side of the heart while being substantially atraumatic to minimize damage to the tissue.

In some such embodiments of the present invention, the step of anchoring to maintain access through the target tissue site comprises advancing the device (such as the puncture device 110) through the fossa to the left side of the heat to maintain access to the left side of the heart. The step additionally comprises a step of removing the supporting member 130 [such as dilator 30A] and leaving the puncture device 110 [such as RF guidewire 10] to maintain access to the region of tissue such as the left side of the heart.

As such, in some examples, the step of anchoring comprises removing the supporting member 130 comprising the dilator 30A to enable anchoring by allowing the RF guidewire 10 to remain positioned to maintain access to the eft side of the heart. The sheath 20 may additionally be removed as well.

Using a Puncture Device for Initial Access, Positioning and Puncturing

In some such embodiments of the present invention, the steps of accessing, positioning, puncturing and anchoring are performed using a puncture device.

Alternatives for the Device being Used for Initial Access, Positioning and/or Puncturing—Based on the Base Claim these Dependents Depend from In some such embodiments of the present invention, the device comprises a flexible puncture device 112 where one or more of the steps of accessing, positioning, puncturing and anchoring are performed using the flexible puncture device 112. In some such examples, each of the steps of accessing, positioning, puncturing and anchoring are substantially performed using the flexible puncture device 112.

In some such embodiments of the present invention, the device comprises a substantially flexible guidewire (such as a mechanical guidewire 118 or an RF guidewire 10) where one or more of the steps of accessing, positioning, puncturing and anchoring are performed using the substantially flexible guidewire (such as a mechanical guidewire 118 or an RF guidewire 10). In some such examples, each of the steps of accessing, positioning, puncturing and anchoring are substantially performed using substantially flexible guidewire (such as a mechanical guidewire 118 or an RF guidewire 10).

In some such embodiments of the present invention, the device comprises a flexible energy based puncture device 114 where one or more of the steps of accessing, positioning, puncturing and anchoring the steps are performed using the flexible energy based puncture device 114. In some such examples, each of the steps of accessing, positioning, puncturing and anchoring are substantially performed substantially using flexible energy based puncture device 114.

In some such embodiments of the present invention, the device comprises a flexible RF guidewire 10 and wherein one or more of the steps of accessing, positioning, puncturing and anchoring are performed using the flexible RF guidewire 10. In some such examples, each of the steps of accessing, positioning, puncturing and anchoring are substantially performed substantially using flexible the flexible RF guidewire 10.

In some such embodiments of the present invention, wherein the device comprises a flexible mechanical guidewire 118 having a relatively sharp distal tip 18*d* wherein one or more of the steps of accessing, positioning, puncturing and anchoring are performed using the flexible mechanical guidewire 118. In some such examples, each of the steps of accessing, positioning, puncturing and anchoring are substantially performed substantially using flexible mechanical guidewire 118.

Repeating Steps of Accessing and Positioning

In some such embodiments of the present invention, the method further comprises repeating the steps of accessing [1], shown in FIG. 2B, and positioning [3] as shown in FIG. 2D, until the device (such as the puncture device 110) is positioned at the desired target tissue site prior to the step of puncturing [4], as shown in FIG. 2E.

Reshaping the Supporting Member

In some such examples, repeating the step of positioning [3] as shown in FIG. 2D, further comprises reshaping a curvature of the supporting member 130 after removing the supporting member 130, and re-tracking [2] the supporting member 130 over the device, as shown in FIG. 2C (such as the puncture device 110 that has been re-positioned [1] within the SVC as shown in FIG. 2B), prior to repeating the step of positioning as shown in FIG. 2D, which in the example shown comprises a drop-down procedure to find the fossa 504. In a specific example, the supporting member 130 comprises a reinforcing member 34, where the step of positioning is performed using the reinforcing member 34.

In some such embodiments of the present invention, the method comprises reshaping the supporting member 130 (such as the reinforced dilator 30A). In some such examples, the method comprises pulling the dilator element or dilator 30A out and reshaping it. In other examples, comprises pulling both the dilator element 30A and the sheath 20 out and reshaping it.

Supporting Member Comprises Reinforced Dilator

In some such examples re-shaping is performed using the supporting member 130 comprising a reinforced dilator 30A where the reinforced dilator 30A comprises the reinforcing member 34, where the step of positioning is performed using the reinforced dilator 30A that can be re-shaped.

Supporting Member Comprises a Stylet

In some embodiments, alternatively, as discussed further herein below, with respect to FIGS. 4A-4E, the step of re-shaping can be performed using the supporting member 130 comprising a stylet 60 wherein the stylet 60 is the reinforcing member 34, and the step of positioning is performed using the stylet 60.

In some such examples, the stylet element 60 can be taken out and reshaped. In other examples, the stylet element 60 along with the sheath 20 and/or dilator 30B may be pulled out and re-shaped to see what the net shape might be and then can be re-inserted therein.

The methods outlined herein above may also be used for embodiments discussed further herein below having a removable stylet 60, as shown in FIGS. 4A-4E and FIGS. 6A-6H.

Mapping System to Visualize Initial Access Tracking and Positioning

In some such embodiments with respect to FIGS. 2A-2G, and also additionally with reference to embodiments shown in FIGS. 4A-4E and FIGS. 6A-6H, the step of positioning is performed using a flexible RF guidewire 10. In some such examples, the steps of positioning, and puncturing are performed using a flexible RF guidewire 10. Still additionally, in some such examples, the steps of positioning, puncturing and anchoring are performed using a flexible RF guidewire 10. In some such examples, a mapping system as provided below may be used to visualize the steps of positioning and anchoring. In some such examples, as provided in FIGS. 2A-2G and FIGS. 4A-4E, the step of accessing may additionally be performed using the RF guidewire 10. As such, in some such examples, a mapping system as provided below may be used to visualize the flexible RF guidewire 10 using a mapping system during the steps of accessing positioning and anchoring. In some such examples, the method further comprises the step of visualizing the flexible RF guidewire 10 using a mapping system during the steps of accessing and positioning.

As such embodiments of the present invention provide a mapping system that is usable to visualize an RF guidewire 10 during a method of puncturing tissue during one or more of the steps of accessing, positioning and anchoring.

In some instances, the mapping device comprises an electro-anatomical mapping system where the electro-anatomical mapping system may be magnetic or impedance based to create virtual volumes. In some examples, the electro-anatomical mapping system is usable with other echocardiographic imaging modalities, which may be ultrasound. The echocardiographic imaging modalities may be used as an overlay in maps, in other words they may be used provide additional information to the mapping system. The echocardiographic imaging modalities may comprise intracardiac cardiography or TEE echorcardiographic In some examples, the method involves switching between a mapping mode that is used for each of the steps of accessing, positioning, and anchoring and the puncture mode that is used for the step of puncturing.

In some such examples, the method of mapping the RF guidewire 10 to visualize using an imaging modality, may be usable with a flexible wire with an electrode which may or may not deliver energy which may be used for recording purposive. In some cases it may be a passive electrode for recording purposes. Alternatively as discussed above, if an RF guidewire 10 is used, then the mapping system is usable with an active electrode such as the distal electrode tip 10d of the RF guidewire 10. As such the recording and mapping properties of a mapping system, are usable with a guidewire having a passive electrode or an active electrode. In a specific example, where a wire is provided with a passive electrode for mapping, the wire may comprise a puncturing means or a means to puncture tissue. In one instance the wire may comprise a mechanical guidewire 118 that may have a sharp distal tip 118d for puncturing tissue.

In some such embodiments the reinforcing member is the stylet 60 that is usable independently from the substantially flexible energy based puncture device 114 such as an RF wire 10.

As a general overview, in one broad embodiment, with respect again to FIG. 2A-2G, a method is provided for carrying out a transseptal puncture, the method comprising: (i) Advancing the RF wire into the superior vena cava, as shown in FIG. 2B, (ii) advancing the sheath and dilator over the wire into the superior vena cava, as shown in FIG. 2C; (iii) withdrawing the RF wire into the dilator, as shown in FIG. 2D; (iv) drop down from the SVC into the heart to find the fossa, as additionally shown in FIG. 2D; (v) tenting with the dilator, (vi) advancing RF wire to puncture position, also with reference to FIG. 2D; (vii) puncturing and advancing RF wire, as shown in FIG. 2E; and (viii) crossing the sheath and dilator over the RF wire, as shown in FIG. 2F.

More specifically, in a specific embodiment of a method of the present invention, with reference again to FIG. 2A, a method is provided for carrying out a transseptal puncture procedure using an assembly 100 comprising a flexible RF wire 10, a sheath 20, and a dilator 30A, the method comprises the following steps: at step 202, [1] advancing the RF wire into the superior vena cava (SVC) to gain access, as additionally illustrated in FIG. 2B. In some such embodiments, providing the energy delivery component (flexible RF wire) separately from the reinforcing member allows the energy delivery component to be used as an access wire. More specifically, the dilator 30A can be advanced later, allowing the flexible RF wire to provide access to the SVC without the use of an additional access wire. This may help reduce the number of steps and streamline the procedure, and as such may reduce procedural time and complexity.

The method additionally comprises the following steps: at step 204, [2] advancing the sheath 20 and dilator 30A combination over the flexible RF wire into the SVC. Thus, the flexible RF wire 10 functions as an access wire and enables the sheath 20 and dilator 30A (for example as an assembly) to be tracked over the flexible RF wire 10 into the SVC as shown in FIG. 2C.

The method additionally provides: at step 206, withdrawing the RF wire into the dilator 30A and step 208, [3] performing a drop down from the SVC into the heart to locate the fossa, as shown in FIG. 2D for carrying out the step of positioning the assembly 100. In one such example, having the reinforced member 34 (within the dilator 30A) as separate from and operable independently form the flexible RF wire provides the additional advantage of allowing the drop down to be repeated if the fossa is missed in the first pass. More specifically, it eliminates the need to re-wire, in other words to re-insert an access wire, remove the access wire and then re-advance a rigid puncture device such as a needle into the SVC in order to repeat the drop down. More specifically, in an embodiment of the instant application, the dilator 30A (and thus the reinforcing member 34) may be partially removed or retracted along with the sheath 20 and the flexible RF wire 10 may be re-advanced into the SVC. The sheath 20 and the dilator 30 may then be re-advanced over the flexible RF wire 10, as shown in FIG. 2C and the drop down may be repeated to allow the RF wire 10 to engage the fossa. This may help reduce procedural time and increase safety as an additional exchange is not required. Adding an additional exchange may add more time and add unnecessary risk. Thus, procedural time and risk may be reduced with the current embodiments where the energy delivery component and the rigid component are decoupled.

The reinforcing member 34 [within the dilator 30A] provides the additional advantage of providing sufficient stiffness to the assembly 100 to facilitate the drop down, at step 208. As such the reinforcing member 34 enables sufficient force transmission and torque to allow the assembly 100 to engage the septum, as illustrated in FIG. 2D. The method further comprises: at step 212 tenting with the dilator 30A, with reference to FIG. 2D. The reinforcing member 34 provides sufficient stiffness to the assembly 100 to enable force to be imparted to the distal end of the assembly 100, thus enabling tenting with the dilator 30A. In some examples, having the reinforcing member 34 within the dilator 30A, allows it to be removed and re-shaped to allow for optimizing the position against the fossa. In some such embodiments, prior to the step of tenting, at step 210, the physician may assess whether the angle of the dilator 30A and/or the assembly 100 is sufficient. If the angle is not deemed to be sufficient, at step 211, the physician may pull out the dilator 30A and reshape the curve. The dilator may be then be reinserted as indicated by step 213. The procedure then may be repeated starting at step 210, and a drop down may be performed again using the assembly 100. Once the fossa has been located, the physician may proceed with the step of tenting with the dilator, at step 212.

The method additionally comprises the steps of: at step 214, advancing RF wire 10 to puncture position and at step 216 [4] puncturing and advancing RF wire 10, as shown in FIG. 2E. The advancement of the RF wire 10 into the left side of the heart 500, enables anchoring of the RF wire 10 on the left side of the heart to maintain access to the left side of the heart. The flexible RF wire 10 may provide the additional advantage of allowing the operator to push hard without injury as the flexible RF wire is more flexible. The method additionally comprises: at step 218, [5] crossing the sheath and dilator over the RF wire 10, as additionally shown in FIG. 2F. The flexible RF wire 10 may additionally protect the open end of the sheath 20/dilator 30A so it does not push hard into the tissue. At step 218, the sheath 20 and dilator 30A [including the reinforcing component 34] may then be removed.

As outlined herein, energy delivery component is provided as a flexible RF wire 10 that is separate from a stiff component such as a reinforcing member 34 [provided within the dilator 30A], where the reinforcing member 34 [with the dilator 30A] is separable from and removable from the flexible RF wire 10. This provides the additional advantage, in that the reinforcing member 34 [within dilator 30A] may be removable after transseptal puncture and access, providing a step [6] of allowing the flexible RF wire 10 to remain positioned within the left atrium which allows for immediate anchoring of the flexible RF wire within the left atrium, as shown in FIG. 2G. In one such example, the RF wire may be positioned within the left superior pulmonary vein for anchoring. This may enable the RF wire to maintain access into the left atrium, allowing removal of the reinforcing member 34 [along with dilator 30A to facilitate exchange of devices into the left atrium using the flexible RF wire. This may additionally reduce an additional exchange of the left side as it may eliminate the need for the physician to advance another wire after puncture to maintain access on the left side for tracking additional devices into the left side. An additional benefit of minimizing exchanges on the left side, in addition to reducing procedural time and the number of steps required, is minimizing risk of infection, embolisms and stroke. In another example, the RF wire 10 may have a pigtail curve at the distal end. This may enable anchoring of the RF wire 10 in the left atrium instead of the pulmonary vein. Alternatively, the RF wire 10 may be used to anchor in the pulmonary vein. In some such examples, the former method of anchoring in the left atrium may provide additional advantages not found in the latter method.

Example 1 [Reinforced Dilator]

In some embodiments of the present invention, in summary, a method is disclosed for puncturing tissue, the method comprising the steps of: advancing a flexible puncture device 112 into a region of tissue; advancing a sheath 20 and supporting member 130 over the flexible puncture device 112 into the region of tissue; withdrawing the flexible puncture device into the supporting member 130; positioning the assembly 100 at a target tissue site in the region of tissue; tenting with the supporting member 130; advancing the flexible puncture device 112 to puncture position; puncturing and advancing flexible puncture device 112; and crossing the sheath 20 and dilator 30A over the flexible puncture device.

In some such examples, as above, the method of puncturing tissue comprises a method for carrying out a transseptal puncture, wherein the region of tissue comprises the superior vena cava. In some examples, the flexible puncture device comprises an RF guidewire 10 and the supporting member comprises a reinforced dilator 30A.

Some such embodiments of the present invention comprise a method for carrying out a transseptal puncture, comprising the steps of: advancing the RF guidewire into the superior vena cava; advancing a sheath and dilator over the RF guidewire into the superior vena cava; withdrawing the RF guidewire into the dilator, dropping down from the superior vena cava into the heart to find the fossa; tenting with the dilator, advancing the RF guidewire to puncture position; puncturing using the RF guidewire and advancing the RF guidewire; and crossing the sheath and dilator over the RF wire.

Example 2

In another example, embodiments of the present invention provides an assembly 300, as shown in FIG. 3A, for puncturing tissue (such as creating a transseptal puncture through a septum of a heart). Similar to embodiments described herein above, the assembly 300 provides a puncture device such as a substantially flexible energy delivery puncture device 114 for puncturing tissue via delivery of energy (such as flexible RF guidewire 10 and a supporting member for supporting the substantially flexible energy delivery puncture device, such as a separate reinforcing member 34. In some such examples, the supporting member comprises a reinforcing member 34. In some such embodiments, the substantially flexible energy delivery puncture device 114 (such as RF guidewire 10) is capable of being selectively insertable within the supporting member 130 to be selectively usable in co-operation therewith during a portion of the procedure and wherein the substantially flexible energy delivery puncture device 114 (such as RF guidewire 10) is usable independently therefrom during another portion of the procedure, in order to facilitate exchange and positioning while providing substantially atraumatic puncture of tissue. Device In one such example, as illustrated in FIG. 3A, the assembly 300 comprises a flexible energy delivery component 114 that is provided separately from and is operable independently from a supporting member. In one such example, the flexible energy delivery component comprises an RF wire 10, and the separate supporting member 130 comprises a stylet 60 that defines a reinforcing member 34. In other words, as provided herein below the supporting member 130 is the reinforcing member 34 that is provided as a stylet 60 that is usable independently from a puncture device 110 such as a flexible puncture device 112. In still others words, the supporting member 130 is defined by the reinforcing member 34, where in one example, the reinforcing member 34 comprises the stylet 60. The assembly 300 additionally comprises a sheath 20 and a dilator 30B that are usable with the flexible RF wire 10. In the particular example shown the reinforcing member 64 is also provided separately from and removable from the dilator 30B which in the present embodiment is provided as a flexible dilator.

Some such embodiments comprises a dilator 30B that is usable with the supporting member 130) to form a supporting member assembly 134 for selective use there-with during a portion of the procedure, as shown in FIG. 3B. In some such embodiments, as noted above, the supporting member 130 comprises a stylet 60 defining the reinforcing member 34. In some examples, a dilator 30B is provided that is usable with the stylet 60) for selective use there-with to form a stylet assembly 164, as shown in FIG. 3C.

In some such embodiments, the puncture device 110 comprises a substantially flexible energy based puncture device 114. In a specific instance of this example, the substantially flexible energy based puncture device 114 comprises a flexible RF guidewire or wire 10. In some embodiments, the RF guidewire 10 is capable of being selectively usable in co-operation with the stylet 60 (for example by being selectively being coupled thereto) during a portion of the procedure, and the RF guidewire 10 is usable independently from the stylet 60 during another portion of the procedure. Where selective use of the RF guidewire 10 in conjunction with the stylet, as well as without the stylet 60, facilitates puncture of tissue.

Supporting Member/Reinforcing Member Shape-Ability

In some such embodiments of the present invention where the supporting member 130 is provided separately from a dilator 30B, the assembly 300 provides a supporting member 130 that is shapeable to enable it to be removed from the puncture device 110 (such as a flexible tissue puncture device 112, for e.g. a substantially flexible energy based tissue puncture device 114) to enable a curve of the supporting member 130 be re-shaped to be reinserted therewith. For example, the re-shaped supporting member 130 is re-insertable with and/or usable with the substantially flexible energy based tissue puncture device 114 and/or one or more other components of the assembly 300 such as dilator 30B and/or sheath 20), in order to optimize the position of the assembly 300 against a target tissue site to facilitate puncture (such as a fossa of the heart to facilitate a transseptal puncture).

In a specific example, the stylet 60 is shapeable to enable the stylet 60 to be removed from the substantially flexible puncture device to enable a curve of the stylet 60 be re-shaped to be reinserted therewith, in order to optimize the position of the assembly against a target tissue site. In some such examples, the stylet 60 is removable from the one or more components or member of the assembly 300 to be re-shaped to be re-inserted therewith to position the assembly 300 at the target tissue site. Details of the stylet 60 defining the reinforcing member 34 in use with a dilator 30B and flexible RF wire 10 are shown in FIGS. 3B and 3C. More specifically, FIGS. 3B and 3C, illustrate a dilator 30B which in some examples is a flexible dilator such as a standard transseptal dilator without having a reinforcing member embedded therein or in other words separately from the dilator 30B, the dilator 30B comprising a proximal portion 31 that terminates at a distal tip 41. In some embodiments, the dilator 30B may additionally include a radiopaque marker 42 at the distal tip 41. Similar to embodiments disclosed herein above, the dilator 30B comprises a dilator shaft 32 that extends along the proximal portion 31. However, unlike embodiments discussed herein above, assembly 300 provides a reinforcing member or component 34 defined by stylet 60 that is provided separately from the dilator 30B, and functions as a removable reinforcing member that is removable from the dilator 30B. As such, the reinforcing member 34 is provided separately from and is removable from both the flexible RF wire 10 and the dilator 30B. FIG. 3B shows the assembly 300 in position for a drop down, whereas FIG. 3C shows the assembly 300 in position for arcing to enable the transseptal puncture.

Atraumatic Stylet

Figure 5A:
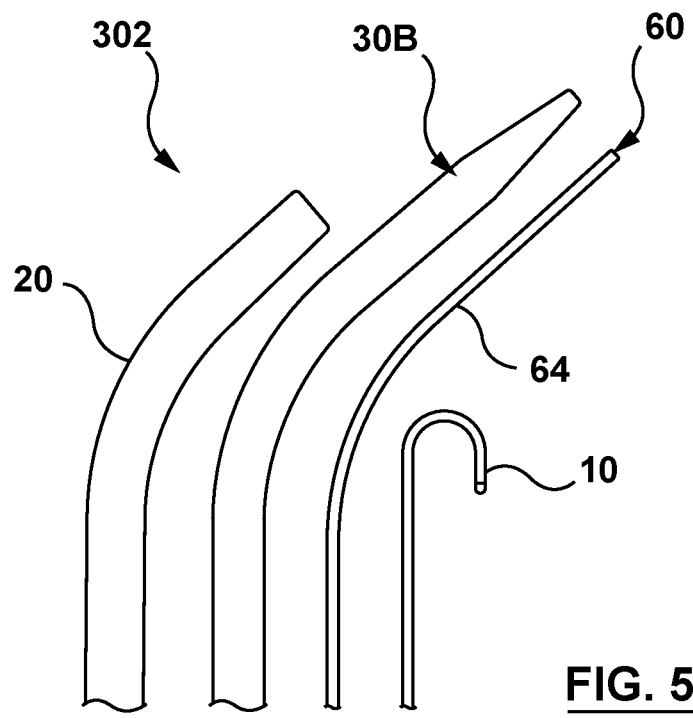
FIG. 5A is an illustration of a transseptal assembly in accordance with a further embodiment of the present invention.
Figure 5B:
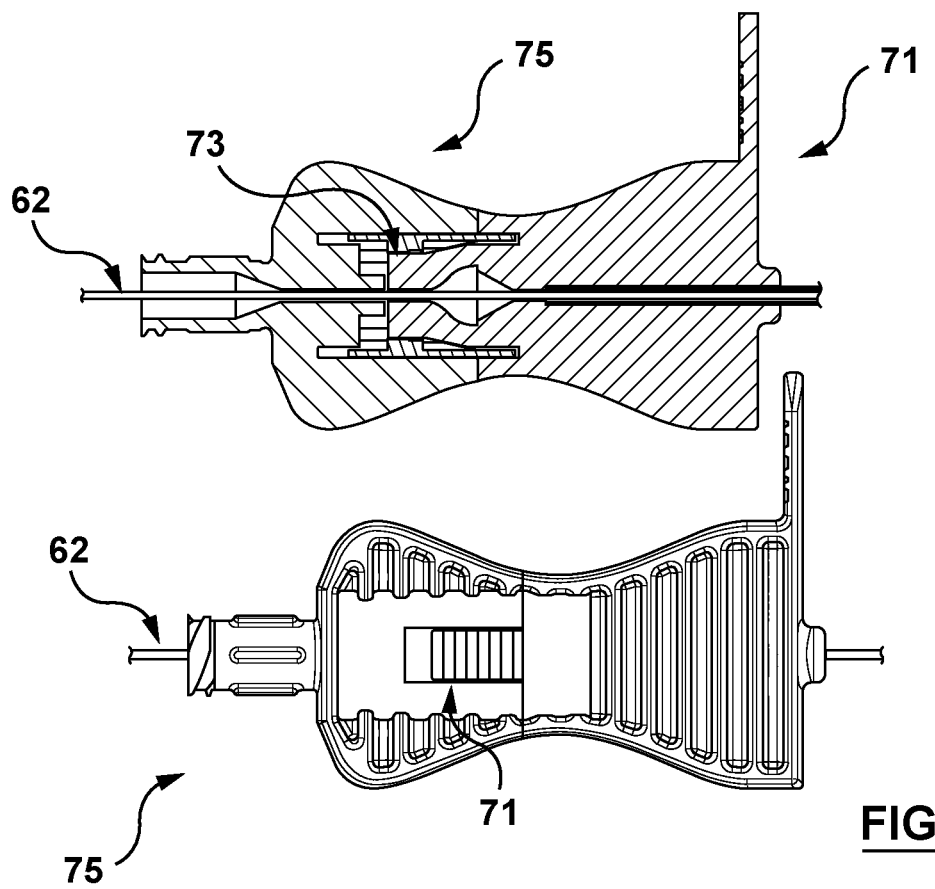
FIG. 5B shows a locking mechanism for enabling coupling of a stylet and RF wire during use, in accordance with an embodiment of the present invention.
Figure 5C:
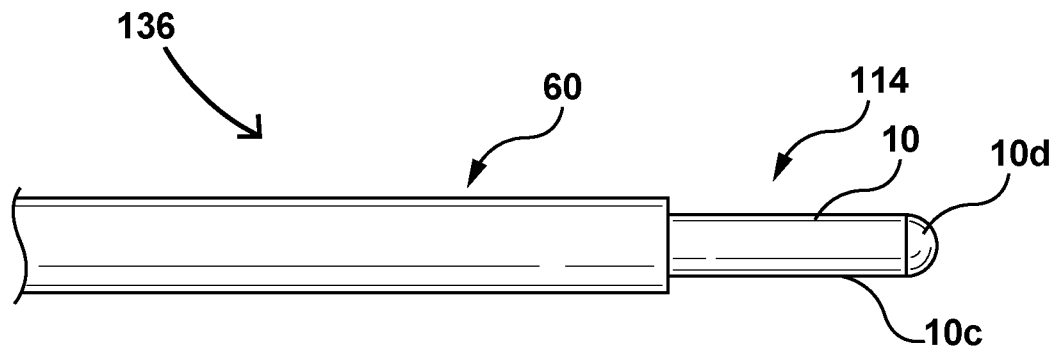
FIG. 5C shows a stylet and RF wire in a locked position, in accordance with a step of an embodiment of a method of the present invention.
Figure 5D:
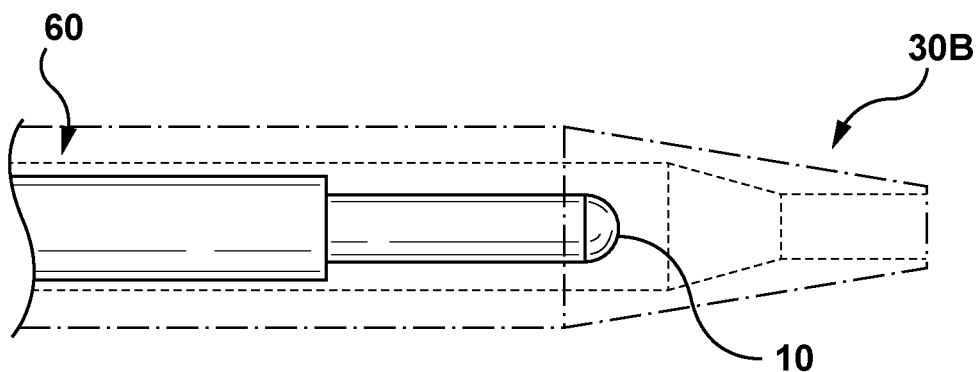
FIG. 5D shows a stylet and RF wire within a dilator for a drop down position, in accordance with a step of a method of the present invention.
Figure 5E:
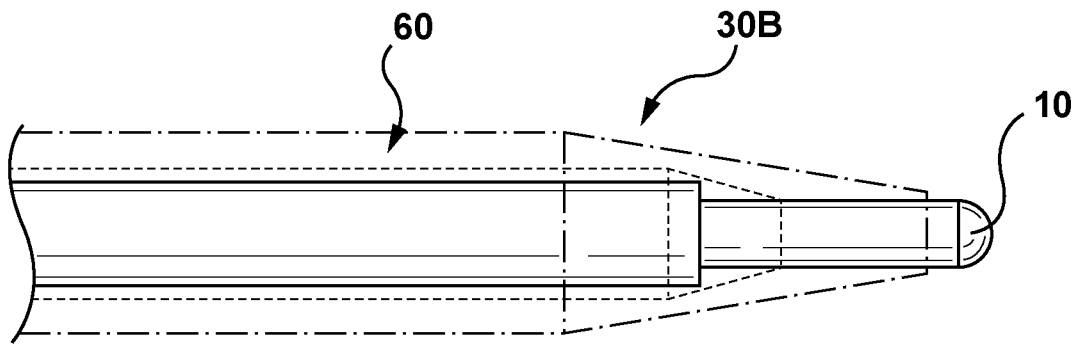
FIG. 5E shows a stylet and RF wire within a dilator in an arcing position, in accordance with a step of a method of an embodiment of the present invention.
Figure 5F:
FIG. 5F shows a stylet and RF wire, in accordance with an alternate embodiment of the present invention.

In some embodiments, the stylet 60 is provided as a substantially atraumatic stylet 68, as shown in FIG. 5F to prevent damage to the dilator 30A that it is inserted in. In some such examples, the stylet 68 comprises a tapered distal tip 69 to prevent and/or help minimize skiving and to provide a smoother feel for the user upon insertion into a dilator during use.

In some embodiments, as an alternative or in addition to providing a tapered distal tip 69, the stylet 60 is made substantially atraumatic by providing a lubricous coating 67 on the stylet 60 in order to prevent and/or help minimize skiving and to provide a smoother feel for the user upon insertion into a dilator during use.

In some such examples, the lubricous coating 67 comprises a PTFE coating. The PTFE coating may be spray coated onto the stylet 60 or it may be provided as a heat shield.

Alignment Using Radiopaque Markers

In some embodiments of the present invention, similar to embodiments discussed previously with respect to assembly 100, the assembly 300 comprises a substantially flexible energy based puncturing device 114 (such as the RF guidewire 10) that comprises one or more device radiopaque markers 12 at a distal end of thereof. Additionally, the supporting member assembly comprises one or more supporting assembly radiopaque markers 42 at the distal end of a supporting member assembly 134 (for example comprising a separate reinforcing member 34 such as a stylet 60 and a puncture device 110 such as a substantially flexible energy based puncturing device 114. In one such example, the supporting assembly radiopaque marker 42 is provided on the dilator 30B of the supporting member assembly 134. In some such examples, the one or more device radiopaque markers 12 are configured to co-operate with the supporting assembly radiopaque marker 42 to indicate the relative position of the substantially flexible energy based puncturing device 114.

In some such embodiments, the assembly 300) comprises an initial configuration 100A, where the substantially flexible energy based puncturing device 114 (such as an RF guidewire 10) is positionable within the supporting member assembly 134 such that the one or more device radiopaque markers 12 are not in alignment with the supporting assembly radiopaque marker 42, as shown in FIG. 3A. In some such examples, multiple radiopaque markers may be visible under imaging, including the one or more device radiopaque markers 12 and the supporting member radiopaque marker 42.

The assembly 300 additionally has a first configuration 100B, where the substantially flexible energy based puncturing device 114 is positionable within the supporting member assembly 134 such that the one or more device radiopaque markers 12 are in alignment with the supporting assembly radiopaque marker 42. In some such examples, a single radiopaque marker may be visible under imaging [including the one or more device radiopaque markers 12 and the supporting member radiopaque marker 42 that may be arranged in close proximity to one another].

The assembly 300 additionally has a second configuration 100B, where the substantially flexible energy based puncturing device 114 (such as RF guidewire 10) is positionable/advanceable within the supporting member assembly 134 such that the one or more device radiopaque markers 12 are substantially not in alignment/misaligned with the supporting assembly radiopaque marker 42. In some such examples, the misalignment of the one or more device radiopaque markers 12 with the supporting assembly radiopaque marker 42 indicates positioning of an energy delivery portion 114 (such as electrode distal tip 10*d* or also referred to as distal electrode tip 10*d*) of the flexible energy based puncturing device 114 (such as an RF guidewire 10) beyond the supporting member assembly 134 (for example distal to the distal tip or end of the supporting member 130) for positioning against a target tissue site for puncture of tissue.

With reference now to FIG. 3A, similar to embodiments shown in FIG. 3A and discussed previously, multiple radiopaque markers may be visible under imaging, including the one or more device radiopaque markers 12 and the supporting member radiopaque marker 42, where the one or more device radiopaque markers 12 are positioned distally to the supporting member radiopaque marker 42, indicating that the distal electrode tip 10d is positioned against a target tissue site (such as the septum of the heart) for puncturing the tissue.

In some embodiments of the present invention, one or members or components of the assembly 300 may be radiopaque to facilitate visualization of the assembly 300. In one such example, the sheath 20 and/or the dilator 30B comprise a radiopaque polymer and the stylet 60 (for example comprising a metal shaft) is radiopaque. As such, in some examples, the stylet 60, sheath 20 and/or the dilator 30B are all radiopaque and thus have radiopaque properties. In a specific example, the polymers forming the sheath 20 and/or dilator 30B comprise radiopaque filler such as barium sulfate 20% to provide contrast with the one or more markers 12, 42 at the distal tip, in order to allow the user to see the sheath 20 and/or the dilator 30B in comparison to the RF guidewire 10. As such, the present configuration may enhance visibility and may allow the user to assertain when the RF guidewire 10 (more specifically the electrode distal tip 10d of the RF guidewire 10) is positioned inside or whether it extends outside or beyond the distal tip of the dilator 30B.

In some embodiments of the transseptal assembly 300, the sheath 20 comprises a standard transseptal sheath, the dilator 30B comprises a standard flexible dilator and the flexible RF wire 10 is provided as an 0.035" wire. In some such examples, the flexible RF wire 10 may be J-tip wire or a pigtail wire. In one particular example, the dilator 30 comprises HDPE. The dilator 30 defines an inner diameter that is sufficient to accommodate the stylet 60. In one example, the stylet 60 that defines the reinforcing member 34 comprises a hypo-tube such as a metal hypo-tube. In a specific example, the stylet 60 comprises a metal hypo-tube that comprises a stainless steel hypotube. In one such example, the stainless steel hypo-tube has an ID of greater than about 0.035".

In some examples, the steerable sheath 20 may be an 8 French (Fr) steerable sheath. Alternatively, an 8.5 Fr steerable sheath 20 may be provided. In some such examples, the steerable sheath 20 may be provided with different curvatures. In a specific example, steerable sheaths 20 may be provided in different curvatures, specifically at angles of: 37, 45, 55, 90, or 135 degrees. In a specific instance of this example, the sheath tubing comprises an inner PTFE liner, a braid and a Pebax outer jacket. In some such embodiments, an 8 French (Fr) dilator 30B is provided that is compatible with an 8 French (Fr) Sheath. Alternatively, an 8.5 (Fr) dilator 30B may be provided that is compatible with an 8 French (Fr) steerable sheath 20. Some such dilators may be provided with a 64 degree curvature and an HDPE shaft. The stylet 60 may be provided as a metal hypotube. In one such instance, the stylet 60 may have an ID of greater than about 0.038" and an OD that is less than about 0.060". The dilator 30A may be provided with a 50 degree or 86 degree curvature. In some examples, materials may include HDPE and a metal hypotube that forms the reinforcing member 34.

In some such examples, the RF wire 10 comprises a 0.035" OD wire and may be a J-tip wire or a pigtail wire. In a specific instance of this example, the RF wire 10 may comprise a stainless steel core with a PTFE coating.

Method

Method [Example 2—Removable Stylet]

Using the Same Device for Initial Track Up/Access and Positioning

Figure 4A:
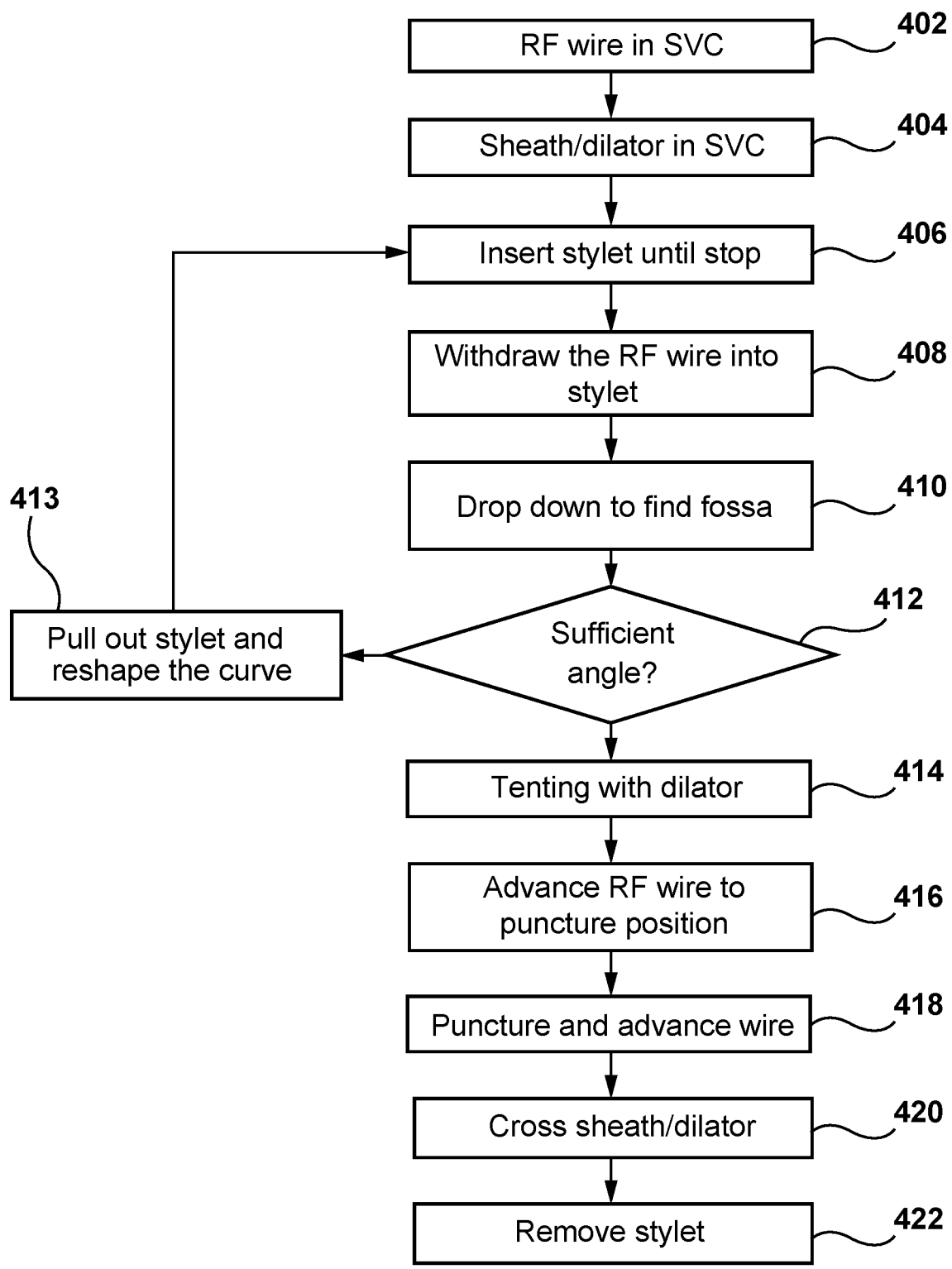
FIG. 4A is an illustration of a flow diagram showing a method of performing a transseptal procedure, in accordance with an alternate embodiment of the present invention.
Figure 4D:
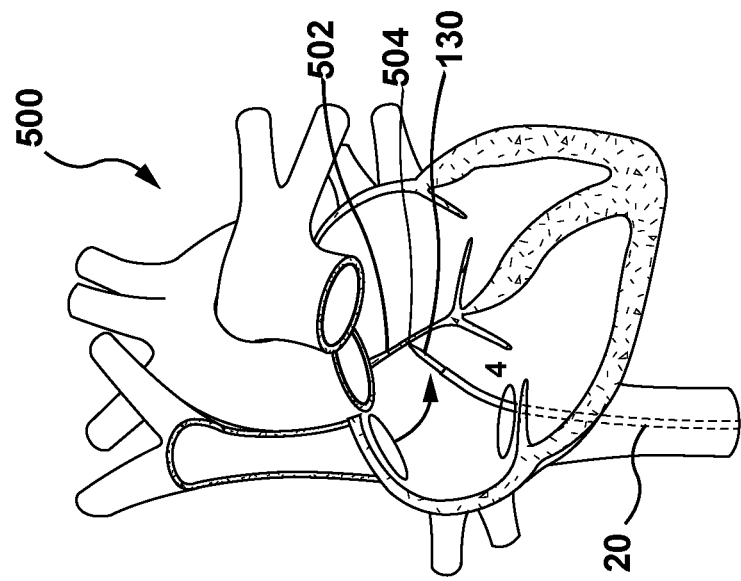
FIGS. 4B-4G illustrate steps of a method of performing a transseptal procedure, in accordance with an alternate embodiment of the present invention.
Figure 4C:
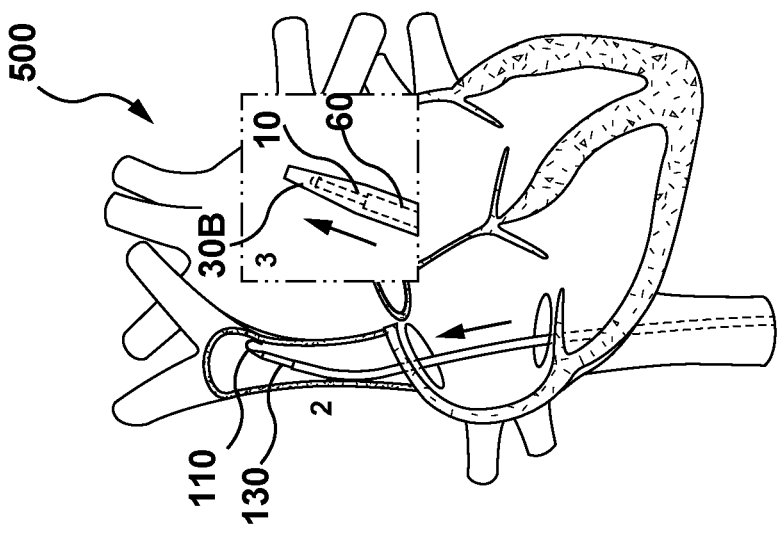
Figure 4B:
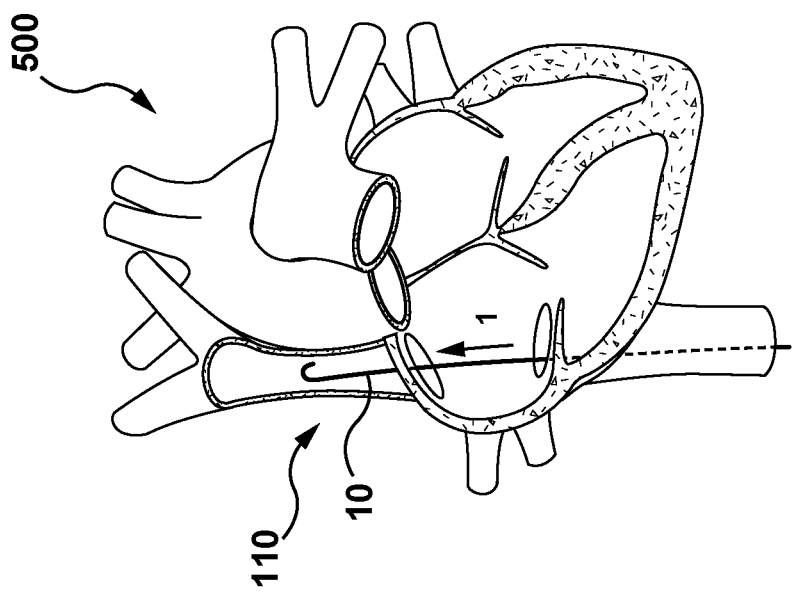

In some embodiments of the present invention, with reference now to FIGS. 4A-4G, a method is disclosed for puncturing tissue. The method comprises the step of: [1] accessing a region of tissue within a patient's body by advancing a device (such as a puncture device 110 such as an RF guidewire 10) into the region of tissue, as shown in FIG. 4B. In some such examples the method of puncturing a region of tissue comprises a method of carrying out a transseptal puncture where the step of accessing the region of tissue comprises advancing the device (such as the puncture device 110) into the superior vena cava (SVC) 501 adjacent a heart 500 of the patient, as shown in FIG. 4B In some embodiments of the present invention, the method for puncturing tissue additionally comprises the step of: [4] positioning a device at a target tissue site in the region of tissue, as shown in FIG. 4D, by for example: [3] first tracking a supporting member 130 over the puncture device 110 to support the device (such as puncture device 110) as shown in FIG. 4C, to [4] enable advancement of the device (such as a puncture device 110) towards a target tissue site in order to position the device at the target tissue site for puncturing, as shown in FIG. 4D.

In some such examples, the step of positioning the puncture device 110 at the target tissue site comprises performing [4] a drop down from the superior vena cava (SVC) into the heart 500 of the patient to locate a fossa ovalis (or fossa) 504 along a septum 502 of the heart 500, by first for example (3) tracking or advancing a supporting member 130 (such as a stylet) over the device (such as a puncture device 110) into the SVC to (3) facilitate the drop down procedure, as shown in FIG. 4D, to position the puncture device 110 at the fossa. For example, this involves dropping down the assembly 300 from the superior vena cava into the heart to find the fossa.

In some examples, the step of positioning [4] is performed by first for example additionally comprises a step of advancing [2] a sheath 20 and dilator 30B over the device (such as RF guidewire 10) into the superior vena cava, prior to tracking and advancing a supporting member 130 which may comprise inserting a stylet 60 in the dilator 30B [for example until it reaches a stop], as shown in FIG. 4C. In some such examples, the step of positioning [4] is performed after a step of withdrawing the RF guidewire into the stylet 60.

In some such examples, as shown in FIGS. 4B-4D, the steps of accessing [1], as shown in FIG. 4B and positioning [4], as shown in FIG. 4D, are performed using the same device such as a puncture device 110, wherein the puncture device 110 is usable without the supporting member 130 [comprising the stylet 60] during the step of accessing [1] and wherein the device is usable with the supporting member 130 [comprising the stylet 60] during the step of positioning [4].

Using a Puncture Device for Initial Access and Positioning

In some such embodiments of the present invention, as shown in FIGS. 4B-4D, the steps of accessing and positioning are performed using a puncture device 110 [such as an RF guidewire 10].

Using the Same Device for Initial Access, Positioning and Puncturing

Figure 4E:
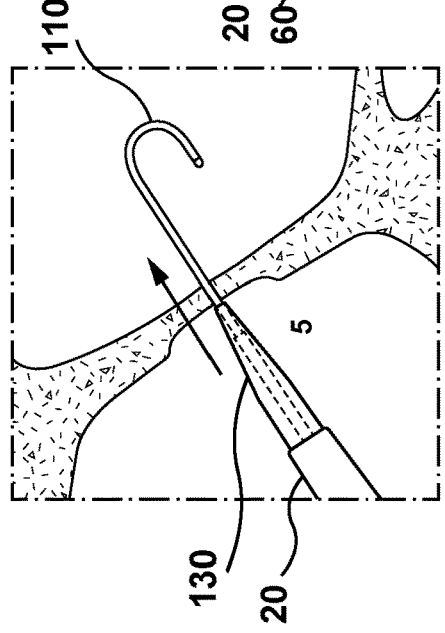

In some such embodiments of the present invention, as shown in FIG. 4E, the method additionally comprises: a step of puncturing[5] through the target tissue site using a device (such as the puncture device 110) after the step of positioning [4] as shown in FIG. 4D. The supporting member 130 [comprising the stylet 60] supports the device (such as puncture device 110) during puncturing [5] where the steps of accessing [1], positioning [4] and puncturing [5] are performed using the same device.

In some embodiments of the present invention, the step [5] of puncturing through the target tissue site comprises the step [5] of puncturing through the fossa 504 to gain access to a left side of the heart 500. This enables one or more devices of the assembly 100, such as the supporting member 130 (such as dilator 30A) and sheath 20 of the assembly 100 to be tracked over the RF guidewire 10 into the left side of the heart.

In some such embodiments, the a step of puncturing [5], is performed by first advancing the device (such as the RF guidewire 10) and tenting with the dilator 30B, as shown in FIG. 4D, to enable the RF guidewire 10 to be advanced to the puncture position, in order to the puncture the septum 502 at the fossa 504.

Using a Puncture Device for Initial Access, Positioning and Puncturing

In some such examples, as shown in FIGS. 2B-2E, the steps of accessing, positioning, and puncturing are performed using a puncture device 110.

Figure 4F:
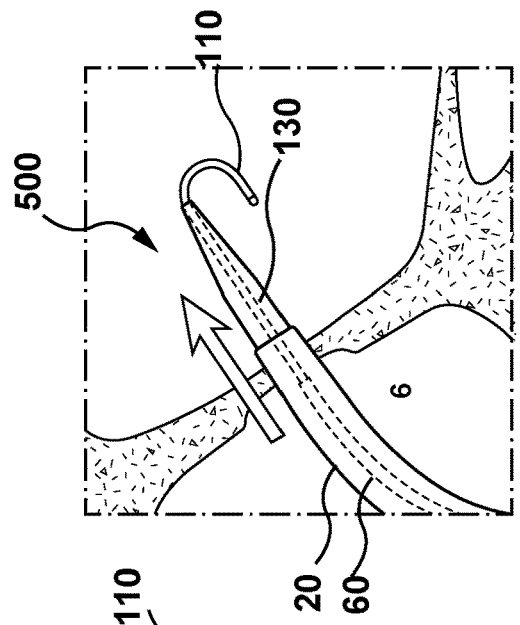
Figure 4G:
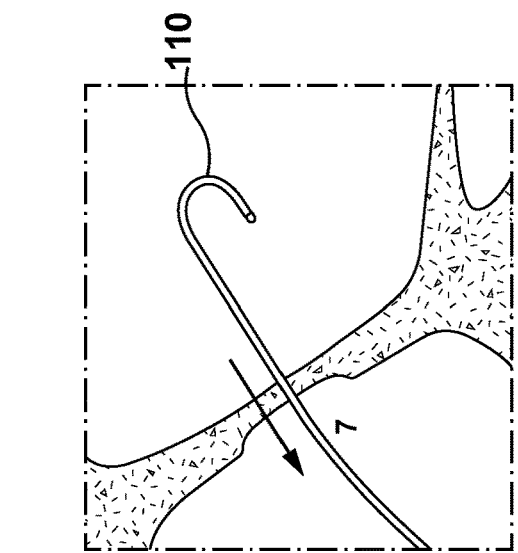

Using the Same Device for Initial Access, Positioning and Puncturing and Anchoring In accordance with an embodiment of the present invention, the method additionally comprises a step of anchoring [6], as shown in FIG. 4E, where the step of anchoring is performed using a device (such as the puncture device 110) after the step of puncturing [5] through the target tissue site, to maintain access through the target tissue site to the other side of the target tissue site, to allow one or more additional device [such as sheath 20 and the dilator 30B] to be advanced or tracked over the device (such as the puncture device 110, for example an RF guidewire 10) in order to allow crossing of the sheath 20 and dilator 30B to the other side of the target tissue site, for example into the left side of the heart, as shown in FIG. 4F, where the steps of accessing [1], positioning [4], puncturing and anchoring [5] are performed using the same device. The RF guidewire 10 may be left to maintain access to the left side of the heart as shown in FIG. 4G. The RF guidewire 10 functions as a rail to guide one more devices to the left side of the heart. In some such examples, the RF guidewire 10 provides a substantially stiff rail to guide the one or more devices to left side of the heart while being substantially atraumatic to minimize damage to the tissue.

In some such embodiments of the present invention, the step of anchoring to maintain access through the target tissue site comprises advancing the device (such as the puncture device 110) through the fossa to the left side of the heat to maintain access to the left side of the heart.

In some such examples, the step of anchoring additionally comprises removing the stylet 60 to enable anchoring by allowing the RF guidewire 10 to remain positioned to maintain access to the eft side of the heart. The sheath 20 and/or the dilator 30B may additionally be removed as well.

In some such embodiments, the steps of accessing, positioning, puncturing and anchoring are performed substantially using the wire such as the RF guidewire and the removable stylet 60.

Using a Puncture Device for Initial Access, Positioning and Puncturing

In some such embodiments of the present invention, the steps of accessing, positioning, puncturing and anchoring are performed using a puncture device (such as a wire comprising an RF guidewire 10) and a removable stylet 60

Alternatives for the Device being Used for Initial Access, Positioning and/or Puncturing—Based on the Base Claim these Dependents Depend from In some such embodiments of the present invention, the device comprises a flexible puncture device 112 where one or more of the steps of accessing, positioning, puncturing and anchoring are performed using the flexible puncture device 112. In some such examples, each of the steps of accessing, positioning, puncturing and anchoring are substantially performed using the flexible puncture device 112.

In some such embodiments of the present invention, the device comprises a substantially flexible guidewire (such as a mechanical guidewire 118 or an RF guidewire 10) where one or more of the steps of accessing, positioning, puncturing and anchoring are performed using the substantially flexible guidewire (such as a mechanical guidewire 118 or an RF guidewire 10). In some such examples, each of the steps of accessing, positioning, puncturing and anchoring are substantially performed using substantially flexible guidewire (such as a mechanical guidewire 118 or an RF guidewire 10).

In some such embodiments of the present invention, the device comprises a flexible energy based puncture device 114 where one or more of the steps of accessing, positioning, puncturing and anchoring the steps are performed using the flexible energy based puncture device 114. In some such examples, each of the steps of accessing, positioning, puncturing and anchoring are substantially performed substantially using flexible energy based puncture device 114.

In some such embodiments of the present invention, the device comprises a flexible RF guidewire 10 and wherein one or more of the steps of accessing, positioning, puncturing and anchoring are performed using the flexible RF guidewire 10. In some such examples, each of the steps of accessing, positioning, puncturing and anchoring are substantially performed substantially using flexible the flexible RF guidewire 10.

In some such embodiments of the present invention, wherein the device comprises a flexible mechanical guidewire 118 having a relatively sharp distal tip 118d wherein one or more of the steps of accessing, positioning, puncturing and anchoring are performed using the flexible mechanical guidewire 118. In some such examples, each of the steps of accessing, positioning, puncturing and anchoring are substantially performed substantially using flexible mechanical guidewire 118.

Repeating Steps of Accessing and Positioning

In some such embodiments of the present invention, the method further comprises repeating the steps of accessing [1], shown in FIG. 4B, and positioning [4] as shown in FIG. 4D, until the device (such as the puncture device 110) is positioned at the desired target tissue site prior to the step of puncturing [5], as shown in FIG. 4E.

Reshaping the Supporting Member

In some such examples, repeating the step of positioning [4] as shown in FIG. 4D, further comprises reshaping a curvature of the supporting member 130 after removing the supporting member 130 [stylet 60], and re-tracking [3] the supporting member 130 [stylet 60] over the device, as shown in FIG. 4C (such as the puncture device 110 that has been re-positioned [1] within the SVC as shown in FIG. 4B), prior to repeating the step of positioning as shown in FIG. 4D, which in the example shown comprises a drop-down procedure to find the fossa 504. In a specific example, the supporting member 130 comprises the stylet 60, where the step of positioning is performed using the stylet 60.

In some such embodiments of the present invention, the method comprises reshaping the supporting member 130 (by pulling the stylet 60 out and re-shaping it).

Supporting Member Comprises a Stylet

In some embodiments, as discussed with respect to FIGS. 4A-4E, the step of re-shaping can be performed using the supporting member 130 comprising a stylet 60 wherein the stylet 60 is the reinforcing member 34, and the step of positioning is performed using the stylet 60.

In some such examples, the stylet element 60 can be taken out and reshaped. In other examples, the stylet element 60 along with the sheath 20 and/or dilator 30B may be pulled out and re-shaped to see what the net shape might be and then can be re-inserted therein.

The methods outlined herein above may also be used for embodiments discussed further herein below having a removable stylet 60, as shown in FIGS. 6A-6H.

Similar to embodiments described herein above, an overall method/workflow is provided that illustrates a method of carrying out a transseptal puncture procedure using an assembly 300, as described above. The method disclosed herein provides one or more advantages associated with an assembly comprising an energy delivery component that is provided separately from the rigid component. Details of the method are provided herein below.

As a general overview, in one broad embodiment, as shown in FIG. 4A-4G, a method is provided for carrying out a transseptal puncture, the method comprising: (i) Advancing the RF wire into the superior vena cava, (ii) advancing the sheath and dilator over the wire into the superior vena cava; (iii) inserting the stylet in the dilator until it reaches a stop; (iv) withdrawing the RF wire into the stylet (v) dropping down from the SVC into the heart to find the fossa; (vi) tenting with the dilator, (vii) advancing RF wire to puncture position; (viii) puncturing and advancing RF wire; and (ix) crossing the sheath and dilator over the RF wire; and (x) remove stylet.

More specifically, with reference again to FIG. 4A, a method is provided for carrying out a transseptal puncture procedure using an assembly 100 comprising a flexible RF wire 10 or RF guidewire 10, a sheath 20, a standard transseptal dilator 30B, and a stylet 60, the method comprises the following steps: at step 402, [1] advancing the RF wire into the superior vena cava (SVC) to gain access, as additionally illustrated in FIG. 4B. As outlined previously, in some such embodiments, providing the energy delivery component (flexible RF wire 10) separately from the reinforcing member 34, allows the energy delivery component to be used as an access wire or starter wire. More specifically, the stylet 60 defining the reinforcing member 34 can be advanced later, allowing the flexible RF wire 10 to provide access to the SVC without the use of an additional access wire. This may help reduce the number of steps and streamline the procedure, and as such may reduce procedural time and complexity.

The method additionally comprises the following steps: [2] at step 404, advancing the sheath 20 and flexible dilator 30B combination over the flexible RF wire into the SVC. As such, in this embodiment also, the flexible RF wire 10 functions as an access wire and enables the sheath 20 and dilator 30B (for example as an assembly) to be tracked over the flexible RF wire 10 into the SVC as shown in FIG. 4C. Furthermore, in one such example a standard transseptal dilator 30B may be provided without an embedded reinforcing member. This may help allow the initial track up of the sheath 20 and dilator 30B to provide a similar feel to the physician as a standard transseptal.

The method additionally provides an additional step: at step 406, [3] inserting the stylet 60 until a stop within the dilator 30B is reached. At step 408, withdrawing the RF wire into the dilator 30B and step 410, providing a step of positioning the assembly 300 by [4] performing a drop down from the SVC into the heart to locate the fossa, as shown in FIG. 4D, in order to position the assembly 300 at the target tissue site such as the fossa 504 along the septum 502 of the heart 500. The reinforcing member 34 [defined by the stylet 60] provides sufficient stiffness to the assembly 100 to facilitate the drop down. As such the reinforcing member 34 enables sufficient force transmission and torque to allow the assembly 100 to engage the septum 502, as illustrated in FIG. 4D.

In one such example, having the reinforced member 34 (as defined by the stylet 60) as separate from and operable independently form the flexible RF wire 10 may additionally assist with repeatability if one or more steps in the procedure need to be repeated. If the initial placement of the flexible RF wire 10 against the septum 502 is not adequate after the drop down, the sheath 20 and dilator 30B along with the stylet 60 [and thus the reinforcing member 34] may be partially removed or partially withdrawn and the flexible RF wire 10 may be repositioned within the superior vena cava (SVC). The sheath 20, dilator 30B and the stylet 60 [and thus the reinforcing member 34] may be re-advanced over the RF wire 10 to provide adequate force transmission and torque to reposition the RF wire 10 against the septum in a drop down, as shown in FIG. 4D, to locate the fossa 504 prior to RF delivery, for example during the step of positioning the assembly 300 at the target tissue site such as the fossa 504. Thus, the reinforcing member 34 and RF wire 10 may help minimize device exchanges by reducing the need for reinserting an exchange wire. This may help reduce procedural time and enhance safety by eliminating an exchange. Thus, procedural time and risk may be reduced with the current embodiments where the energy delivery component and the rigid component are decoupled.

Furthermore, in the embodiment described herein, a removable reinforcing member is provided in that the stylet 60 and thus reinforcing member 34, is removable from and separable from the dilator 30B. By providing a removable stiffening element by way of a removable stylet 60 allows the stylet to impart different curvatures. A variable system is provided where the location of the stylet 60 within the dilator 30B may be adjusted to leverage a more preferential location for positioning against the dilator 30B against the fossa 504. Additionally the stylet 60 may be re-shapeable allowing and may be pulled out and manually reshaped. In some such embodiments, after the drop down has been performed at step 410, the physician may assess whether the angle of the stylet 60 and/or the assembly 300 is sufficient at step 412, prior to tenting. If the angle is not deemed to be sufficient, the physician may pull out the stylet 60 and reshape the curve, at step 422. The procedure then may be repeated starting at step 406 to step 412.

If the angle is deemed to be sufficient, at step 412, the method further comprises: at step 414 tenting with the dilator 30B, with reference to FIG. 4D. The reinforcing member 34 provides sufficient stiffness to the assembly 100 to enable force to be imparted to the distal end of the assembly 100, thus enabling tenting with the dilator 30B. The method additionally comprises the steps of: at step 416, advancing RF wire 10 to puncture position and at step 416 [5] puncturing and advancing RF wire 10, as shown in FIG. 4E to enable the RF wire 10 to puncture through the septum 502, at the fossa 504, to access the left side of the heart, thereby providing a step of anchoring using the RF wire 10. In some such examples, the RF wire 10 thus positioned functions as an anchor to maintain access to the left side of the heart after puncturing. The flexible RF wire 10 may provide the additional advantage of allowing the operator to push hard without injury as the flexible RF wire 10 is more flexible. The method additionally comprises: at step 420, [6] crossing the sheath 10 and dilator 30B with the stylet 60 therein over the RF wire 10, as additionally shown in FIG. 4F. The flexible RF wire 10 may additionally protect the open end of the sheath 20/dilator 30B so it does not push hard into the tissue. At step 422, the sheath 20 and dilator 30 as well as the stylet 60 [and thus the reinforcing member 34 defined thereby] may then be removed.

As outlined herein, energy delivery component is provided as a flexible RF wire 10 that is separate from a stiff component such as a reinforcing member 34 [as provided by stylet 60], where the stylet 60 is separable from and removable from the flexible RF wire 10. This provides the additional advantage, in that the reinforcing member 34 [defined by stylet 60] may be removable after transseptal puncture and access, providing a step [7] allowing the flexible RF wire 10 to remain positioned within the left atrium which allows for immediate anchoring of the flexible RF wire 10 within the left atrium, for example as shown in FIG. 4G. In one such example, the RF wire 10 may be positioned within the left superior pulmonary vein for anchoring. This may enable the RF wire 10 to maintain access into the left atrium, allowing removal of the stylet 60 [and thus the reinforcing member 34] to facilitate exchange of devices into the left atrium using the flexible RF wire 10. This may additionally reduce an additional exchange of the left side as it may eliminate the need for the physician to advance another wire after puncture to maintain access on the left side for tracking additional devices into the left side. As outlined above, the present embodiment also provides an additional benefit of minimizing risk of infection, embolisms and stroke by minimizing exchanges on the left side, in addition to reducing procedural time and the number of steps required.

Example 2 General Overview

Stylet and Separate RF Wire

As such, in summary, in embodiments of the present invention, a method is provided for carrying out a transseptal puncture, the method comprising: advancing an RF guidewire into the superior vena cava; advancing a sheath and dilator over the RF guidewire into the superior vena cava; inserting a stylet in the dilator until it reaches a stop; withdrawing the RF guidewire into the stylet; dropping down from the superior vena cava into the heart to find the fossa; tenting with the dilator, advancing RF wire to puncture position; puncturing and advancing RF wire; crossing the sheath and dilator over the RF wire; and removing the stylet.

Example 3

In another example, embodiments of the present invention provides an assembly 302 for creating a transseptal puncture through a septum of a heart. Similar to embodiments described herein above, the assembly 302 provides a flexible RF wire and a separate reinforcing member.
Device In one such example, as illustrated in FIG. 5A, the assembly 302 is similar to assembly 300 described previously and comprises a flexible energy delivery component that is provided separately from and is operable independently from a supporting member. In some embodiments, assembly 302 is provided as an example of assembly 300. The assembly 302 comprises: an RF wire 10, a stylet 60 defining a reinforcing member 34, a sheath 10 and a standard transseptal dilator 30B, details of which are described herein above. In the particular example shown the reinforcing member 34 is also provided separately from and removable from the dilator 30B as well as the flexible RF wire 10.

In some embodiments of the present invention, with reference now to FIGS. 5A and 5B, the assembly 302 further comprises a locking feature 75 to allow the flexible energy based puncturing device 114 (such as RF guidewire 10) to be coupled to the reinforcing member 34 (such as stylet 60) to form a needle assembly 136 to allow the flexible energy based puncturing device 114 (such as RF guidewire 10) to be selectively usable with the reinforcing member 34, to provide feel of a needle while enabling use of an RF guidewire.

In a specific example, the locking feature 75 of the assembly 302 enables the RF guidewire 10 to be coupled to the stylet 60 to allow the RF guidewire 10 to be selectively usable with the stylet 60, to provide the feel of a needle while enable use of an RF guidewire 10.

In some such examples, the locking feature 75 may enable the wire (such as the RF guidewire 10) and the stylet 60 to be axially locked such that the wire and stylet 60 may be moved back and forth together. In an additional embodiment, the locking feature 75 may additionally provide rotational locking.

The embodiment presented herein provides a means of locking the flexible RF wire 10 and the reinforcing member 34 which allows the combination to provide the feel of a rigid RF needle while enabling the use of an RF wire 10. The combination provides the advantages provided herein above of a decoupled energy delivery system where a flexible energy delivery component such as the RF wire 10 is provided separately from a supporting member 130 such as a reinforcing member 34. More specifically, in one example, as shown in FIG. 5B, the stylet 60 comprises a locking handle 71 that is operable to be coupled to the flexible RF wire 10 along its proximal portion for a part of the procedure. The locking handle 71 comprises locking arms 73 that may be spring biased to allow the locking arms to engage with and lock the RF wire 10 to the stylet 60 in position, thus defining the locking feature 75. In some examples, the stylet 60 and/or the RF wire 10 additionally comprises a marker band 62 to facilitate the relative positioning of the stylet 60/RF wire 10 prior to locking. As such, the stylet handle 71 locks onto the flexible RF wire 10 for alignment.

FIGS. 5C, 5D and 5E, illustrate details of the assembly 302 in use in accordance with various steps of the procedure. More specifically, FIG. 5C illustrates a flexible RF wire 10 positioned within the stylet 60, which in one example, is configured to be assembled and locked outside of the patient. In another example, the stylet 60 and the RF wire 10 may be locked once positioned inside the patient's body. FIG. 5D illustrates the coupled RF wire 10 and stylet 60 assembly, positioned within the dilator 30B for the drop down position which is referred to as a two finger position. FIG. 5E illustrates a stylet 20, RF wire 10 assembly positioned within the dilator 30B in the arcing position.

In some examples, as described above, the steerable sheath 20 may be an 8 Fr steerable sheath. Alternatively, an 8.5 Fr steerable sheath 20 may be provided. In some such examples, the steerable sheath 20 may be provided with different curvatures. In a specific example, steerable sheaths 20 may be provided in different curvatures, specifically at angles of: 37, 45, 55, 90, or 135 degrees. In a specific instance of this example, the sheath tubing comprises an inner PTFE liner, a braid and a Pebax outer jacket. In some such embodiments, an 8 Fr dilator 30B is provided that is compatible with an 8 Fr Sheath. Alternatively, an 8.5 Fr dilator 30B may be provided that is compatible with an 8 Fr steerable sheath 20. Some such dilators may be provided with a 64 degree curvature and an HDPE shaft. The stylet 60 may be provided as a metal hypotube. In one such instance, the stylet 60 may have an ID of greater than about 0.038" and an OD that is less than about 0.060". The dilator 30B may be provided with a 50 degree or 86 degree curvature. In some examples, materials may include HDPE and a metal hypotube that forms the reinforcing member 34. In some such examples, the RF wire 10 comprises a 0.035" OD wire and may be a J-tip wire or a pigtail wire. In a specific instance of this example, the RF wire 10 wire may comprise a stainless steel core with a PTFE coating.

Method

Example 3 [Lockable Stylet and RF Guidewire]

Using the Same Device for Initial Track Up or Access and Positioning

Figure 6A:
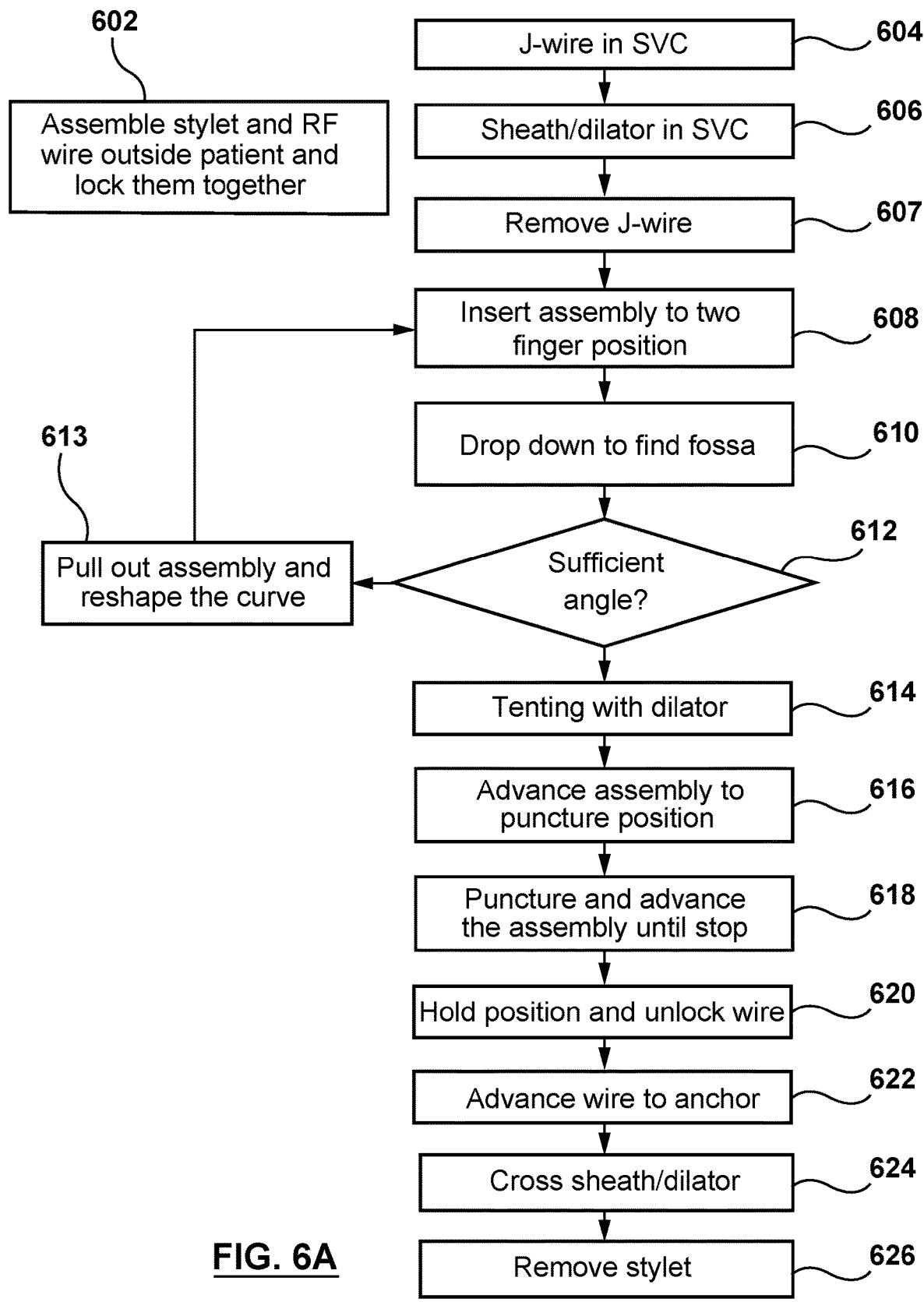
FIG. 6A is an illustration of a flow diagram showing a method of performing a transseptal procedure, in accordance with still another embodiment of the present invention.

In some embodiments of the present invention, with reference now to FIGS. 6A-6H, a method is disclosed for puncturing tissue. The method comprises the step of: [1] accessing a region of tissue within a patient's body by advancing a device (such as a J-wire 101) into the region of tissue, as shown in FIG. 6B. In some such examples the method of puncturing a region of tissue comprises a method of carrying out a transseptal puncture where the step of accessing the region of tissue comprises advancing the device (such as a J-wire 101) into the superior vena cava (SVC) 501 adjacent a heart 500 of the patient, as shown in FIG. 6B.

In some embodiments of the present invention, the method for puncturing tissue additionally comprises the step of: [5] positioning a device at a target tissue site in the region of tissue, as shown in FIG. 6D, by for example by first: [2] advancing a sheath 20 and dilator 30B over the wire (such as a J-wire 101) into the superior vena cava and [3] removing the J-wire; and [4] advancing or tracking a supporting member 130 [comprising a stylet 60] within the dilator. More specifically, the step of [4] advancing or tracking the supporting member comprises a step of [4] inserting a needle assembly within the dilator 30B (for example at a two finger position) within the dilator. The needle assembly comprising a stylet 60 and puncture device 110 such as an RF guidewire 10. In some such examples, the needle assembly comprises a locking feature to lock the RF guidewire 10 to the stylet 60.

The stylet 60 functions to support the device (such as puncture device 110) as shown in FIG. 6C, to [5] enable advancement of the device (such as a puncture device 110) towards a target tissue site in order to position the device at the target tissue site for puncturing, as shown in FIG. 6D.

In some such examples, the step of positioning the puncture device 110 at the target tissue site comprises performing [5] a drop down from the superior vena cava (SVC) into the heart 500 of the patient to locate a fossa ovalis (or fossa) 504 along a septum 502 of the heart 500. For example, this involves dropping down the assembly 300 from the superior vena cava into the heart to find the fossa.

In some examples, a step of withdrawing the RF guidewire into the stylet 60 may not be needed as when the RF guidewire 10 and the stylet 60 are inserted within the dilator 30B in their locked position, the RF guidewire 10 is seated within the dilator 30B.

Using Different or Separate Devices for Accessing and Positioning [Example 3]

As such in some such embodiment, a J-wire is provided and used for the step accessing a region of tissue within a patient's body; and an RF wire 10 is provided and used (which for example is provided as a needle assembly that has an RF wire 10 coupled to a stylet 60) for the step of positioning a device at a target tissue site in the region of tissue by tracking a supporting member (for example as provided as a stylet 60) along with the device (provided as an RF wire 10)] to support the device (such as the RF wire 10) to advance the device (such as the RF wire 10) towards a target tissue site in order to position the device at the target tissue site for puncturing. As such in some examples, the steps of accessing and positioning are performed using different or separate devices (e.g. a J-wire and an RF wire 10, respectively, where the step of accessing is performed without the supporting member (such as stylet 60) and wherein the device (such as an RF wire 10) is usable with the supporting member (such as stylet 60) during the step of positioning.

Using the Same Device for Initial Positioning and Puncturing

In some such embodiments of the present invention, as shown in FIG. 6E, the method additionally comprises: [5] a step of puncturing through the target tissue site using a device (such as the puncture device 110) after the step of positioning [5] as shown in FIG. 6D.

In some embodiments of the present invention, the step [5] of puncturing through the target tissue site comprises the step [5] of puncturing through the fossa 504 to gain access to a left side of the heart 500. In some such embodiments, the step of puncturing [5], is performed by first tenting with the dilator 30B, advancing needle assembly to puncture position, and puncturing and advancing the needle assembly until a stop within the dilator 30B, as shown in FIG. 6E, to enable the RF guidewire 10 to be advanced to the puncture position, in order to the puncture the septum 502 at the fossa 504.

Using a Puncture Device for, Positioning and Puncturing

In some such examples, as shown in FIGS. 6B-6H, the steps of positioning, and puncturing are performed using a puncture device 110.

Using the Same Device for Positioning and Puncturing and Anchoring

In accordance with an embodiment of the present invention, the method additionally comprises a step of anchoring

[6], as shown in FIG. 6F, where the step of anchoring is performed using a device (such as the puncture device 110) after the step of puncturing [5] through the target tissue site, to maintain access through the target tissue site to the other side of the target tissue site, to allow one or more additional device [such as sheath 20 and the dilator 30B] to be advanced or tracked over the device (such as the puncture device 110, for example an RF guidewire 10) in order to allow crossing of the sheath 20 and dilator 30B to the other side of the target tissue site, for example into the left side of the heart, as shown in FIG. 6G, where the steps of positioning, puncturing and anchoring are performed using the same device.

In some such examples, the step of anchoring as shown in FIG. 6F, is performed by first holding the position of the assembly including the needle assembly and unlocking the RF guidewire from the stylet 60 and advancing the RF guidewire to anchor. The method additionally comprises crossing the sheath 20 and dilator 30B over the RF guidewire 10, and removing the stylet 60 as shown in FIG. 6G.

In some such embodiments of the present invention, the step of anchoring to maintain access through the target tissue site comprises advancing the device (such as the puncture device 110) through the fossa to the left side of the heat to maintain access to the left side of the heart.

In some such examples, the step of anchoring additionally comprises removing the stylet 60 to enable anchoring by allowing the RF guidewire 10 to remain positioned to maintain access to the eft side of the heart. The sheath 20 and/or the dilator 30B may additionally be removed as well. In some such embodiments, the steps of accessing, positioning, puncturing and anchoring are performed substantially using the wire such as the RF guidewire and the removable stylet 60. The puncture device 110 can be left to maintain access to the left side of the heart as shown in FIG. 6H. The RF guidewire 10 functions as a rail to guide one more devices to the left side of the heart. In some such examples, the RF guidewire 10 provides a substantially stiff rail to guide the one or more devices to left side of the heart while being substantially atraumatic to minimize damage to the tissue.

Using a Puncture Device for Positioning, Puncturing and Anchoring

In some such embodiments of the present invention, the steps of positioning, puncturing and anchoring are performed using a puncture device (such as a wire comprising an RF guidewire 10) and a removable stylet 60 of the needle assembly.

Alternatives for the Device being Used for Positioning and/or Puncturing, and Anchoring In some such embodiments of the present invention, the device comprises a flexible puncture device 112 where one or more of the steps of positioning, puncturing and anchoring are performed using the flexible puncture device 112. In some such examples, each of the steps of positioning, puncturing and anchoring are substantially performed using the flexible puncture device 112.

In some such embodiments of the present invention, the device comprises a substantially flexible guidewire (such as a mechanical guidewire 118 or an RF guidewire 10) where one or more of the steps of positioning, puncturing and anchoring are performed using the substantially flexible guidewire (such as a mechanical guidewire 118 or an RF guidewire 10). In some such examples, each of the steps of positioning, puncturing and anchoring are substantially performed using substantially flexible guidewire (such as a mechanical guidewire 118 or an RF guidewire 10).

In some such embodiments of the present invention, the device comprises a flexible energy based puncture device 114 where on or more of the steps of positioning, puncturing and anchoring the steps are performed using the flexible energy based puncture device 114. In some such examples, each of the steps of positioning, puncturing and anchoring are substantially performed substantially using flexible energy based puncture device 114.

In some such embodiments of the present invention, the device comprises a flexible RF guidewire 10 and wherein one or more of the steps of positioning, puncturing and anchoring are performed using the flexible RF guidewire 10. In some such examples, each of the steps of positioning, puncturing and anchoring are substantially performed substantially using flexible the flexible RF guidewire 10.

In some such embodiments of the present invention, wherein the device comprises a flexible mechanical guidewire 118 having a relatively sharp distal tip 118d wherein one or more of the steps of positioning, puncturing and anchoring are performed using the flexible mechanical guidewire 118. In some such examples, each of the steps of positioning, puncturing and anchoring are substantially performed substantially using flexible mechanical guidewire 118.

Repeating Steps of Accessing and Positioning

In some such embodiments of the present invention, the method further comprises repeating the steps of accessing [1], shown in FIG. 6B, and positioning [5] as shown in FIG. 8D, until the device (such as the puncture device 110) is positioned at the desired target tissue site prior to the step of puncturing [5], as shown in FIG. 6E.

Reshaping the Supporting Member

In some such examples, repeating the step of positioning [4] as shown in FIG. 6D, further comprises reshaping a curvature of the stylet 60, and re-tracking [4] the stylet 60 as part of the needle assembly [stylet 60 coupled to puncture device] over the device, as shown in FIG. 6C (such as the puncture device 110 that has been re-positioned [1] within the SVC as shown in FIG. 6B), prior to repeating the step of positioning as shown in FIG. 4D, which in the example shown comprises a drop-down procedure to find the fossa 504. In a specific example, the supporting member 130 comprises the stylet 60, where the step of positioning is performed using the stylet 60.

In some such embodiments of the present invention, the method comprises reshaping the supporting member 130 (by pulling the stylet 60 out and re-shaping it) and for example, by unlocking it from the needle assembly.

Supporting Member Comprises a Stylet

In some embodiments, as discussed with respect to FIGS. 6A-6E, the step of re-shaping can be performed the stylet 60 is the reinforcing member 34, and the step of positioning is performed using the stylet 60.

In some such examples, the stylet element 60 can be taken out and reshaped. In other examples, the stylet element 60 along with the sheath 20 and/or dilator 30B may be pulled out and re-shaped to see what the net shape might be and then can be re-inserted therein.

Similar to embodiments described herein above, FIG. 6A illustrates an overall method/workflow for a method of carrying out a transseptal puncture procedure using the assembly 302, as described above. The method disclosed herein provides one or more advantages associated with an assembly comprising an energy delivery component that is provided separately from the rigid component. Details of the method are provided herein below.

General Overview

As a general overview, in one broad embodiment, as shown in FIG. 6A-6H, a method is provided for carrying out a trarnsseptal puncture, the method comprising: (i) Advancing a J-wire into the superior vena cava, (ii) advancing the sheath and dilator over the wire into the superior vena cava; (iii) removing the J-wire; (iv) inserting the stylet/wire assembly within the dilator for the two finger position; (v) dropping down from the SVC into the heart to find the fossa; (vi) tenting with the dilator, (vii) advancing stylet/RF wire assembly to puncture position; (viii) puncturing and advancing the stylet/RF wire assembly until the stop within the dilator, (ix) hold position and unlock RF wire; (x) advance wire to anchor, (xi) crossing the sheath and dilator over the RF wire; and (xii) remove stylet.

More specifically, with reference again to FIG. 6A, a method is provided for carrying out a transseptal puncture procedure using an assembly 302 comprising a flexible RF wire 10, a sheath 20, a standard transseptal dilator 30B, and a stylet 60, the method comprises the following steps: at step 602, assembling stylet and RF wire 10 outside the patient and locking them together; At step 604, [1] advancing the J-wire into the superior vena cava (SVC) to gain access, as additionally illustrated in FIG. 6B. The method additionally comprises the following steps: at step 606, [2] advancing the sheath 20 and flexible dilator 30B combination over the J-wire into the SVC, as shown in FIG. 6C; and at step 607, [3] removing the J-wire. Since a standard transseptal dilator 30B is provided without an embedded reinforcing member, initial track up of the sheath 20 and dilator 30B may provide a similar feel to the physician as a standard transseptal procedure. The method additionally provides an additional step: at step 608, [4] inserting the stylet 60/RF wire 10 assembly 302 to a two finger position, as additionally shown in FIG. 6C. The method additionally comprises: at step 610, [5] performing a drop down from the SVC into the heart 500 to locate the fossa, as shown in FIG. 6D. The stylet 60 defines the reinforcing member 34 and provides sufficient stiffness to the assembly 302 to facilitate the drop down.

In some embodiments of the present disclosure dilator 30B is provided as a standard transseptal dilator 30B. In other embodiments the dilator 30B may be softer or more flexible (or in other words less rigid) than a standard transseptal dilator 30B.

More specifically, the reinforcing member 34 enables sufficient force transmission and torque to allow the assembly 100 to engage the septum, as illustrated in FIG. 6D.

In one such example, similar to the embodiments discussed previously, having the reinforced member 34 (as defined by the stylet 60) as separate from and operable independently form the flexible RF wire 10 may additionally assist with repeatability of aspects of the procedure, if one or more steps in the procedure need to be repeated. If the initial placement of the flexible RF wire 10 against the septum is not adequate after the drop down, the sheath 20 and dilator 30B along with the stylet 60 [after decoupling from the RF wire] may be removed partially or partially retracted and the flexible RF wire 10 may be repositioned within the superior vena cava (SVC) and the drop down procedure may be repeated after re-advancement of the sheath 20/dilator 30B and the stylet 60 may be re-advanced over the RF wire 10 as outlined above.

Furthermore, in the embodiment described herein, a removable reinforcing member is provided in that the stylet 60, and thus reinforcing member 34, is removable from and separable from the dilator 30B. By providing a removable stiffening element by way of a removable stylet 60 may allow the stylet to impart different curvatures. A variable system is provided where the location of the stylet 60 within the dilator 30B may be adjusted to leverage a more preferential location for positioning against the dilator 30B against the fossa. As mentioned previously, the stylet 60 may be re-shapeable allowing and may be pulled out and manually reshaped. In some such embodiments, after the drop down has been performed at step 610, the physician may assess whether the angle of the stylet 60 and/or the assembly 300 is sufficient at step 612, prior to tenting. If the angle is not deemed to be sufficient, the physician may pull out the stylet 60 and reshape the curve, at step 613. The procedure then may be repeated starting at step 608 to step 612.

If the angle is deemed to be sufficient, at step 612, the method further comprises: at step 614 tenting with the dilator 30B. The reinforcing member 34 provides sufficient stiffness to the assembly 100 to enable force to be imparted to the distal end of the assembly 100, thus enabling tenting with the dilator 30B. The method additionally comprises the steps of: at step 616, advancing RF wire 10/stylet 60 assembly to puncture position and at step 618, [6] puncturing and advancing RF wire 10/stylet 60 assembly until the stop within the dilator 30B, as shown in FIG. 6E. The flexible RF wire 10 may provide the additional advantage of allowing the operator to push hard without injury as the flexible RF wire 10 is more flexible.

The method additionally comprises: at step 620, holding the position and unlocking the RF wire 10 from the RF wire 10/stylet 60 assembly, and advancing RF wire 10 to anchor as shown in FIG. 6F. Similar to Example 2, as outlined herein above, with respect to FIGS. 4A-4G, in Example 3, as outlined with respect to FIGS. 6A-6H, a removable reinforcement, the stylet 60 is provided that may facilitate streamlining the procedure. The energy delivery component is provided as a flexible RF wire 10, where the stylet 60 is separable from and removable from the flexible RF wire 10. This provides the additional advantage, in that the RF wire 10 may be advanced independently from the stiffening component, to the left side. The step of [7] positioning of the RF wire 10 and advancement on the left side may provide similar advantages as outlined above for example 2, including anchoring, enhanced safety, minimizing exchanges on the left side, and to facilitate trackability of additional devices. The method additionally comprises the steps of: [8] crossing with the sheath 20/dilator 30B [and stylet 60] on the left side 624 and removing or retracting the stylet at step 626. In some examples, the stylet 60 may cross over to the left side together with the sheath 20 and dilator 30B. Alternatively, the stylet 60 may stay on the right side of the heart while facilitating the sheath 20/dilator 30B to cross through to the left side of the heart. This may provide additional advantages (such as providing atraumaticity during crossing and while maintaining access to the left side) not found in a method where the stylet 60 may cross over to the left side.

As such, in some embodiments, the removable reinforcement may be used in conjunction with but separately from a sheath 20/dilator 30B assembly forming a reinforced support member that is usable in conjunction with the RF wire 10 to facilitate force transmission and torque to ensure engagement with the septum and to facilitate location of the fossa during the drop down procedure. The removable reinforcement [such as stylet 60] may be unlocked from the RF wire 10 removed from the sheath/dilator assembly thereafter leaving the RF wire 10 and in some examples, the sheath and/or dilator to remain positioned within left atrium to facilitate additional device exchanges.

Needle Assembly with Stiffening Member and Flexible Puncture Device

Stiffening Member

As noted above, some embodiment of present invention provide a needle assembly for puncturing tissue, the needle assembly comprises a puncture device 110 flexible puncture device 112 (such as an RF guidewire 10 or a mechanical guidewire 118) for puncturing tissue and a stiffening member (such as a supporting member 130 such as dilator 30A or a reinforcing member 34 such as a stylet 60) for supporting the puncture device, with reference to FIGS. 1A, 1B and 3B-3C. The puncture device is capable of being selectively usable in co-operation with the stiffening member during a portion of the procedure and wherein the puncture device is usable independently therefrom during another portion of the procedure, in order to puncture tissue and to enhance procedural efficiency by facilitating exchange and positioning.

In some such embodiments, as shown in FIG. 1B, the needle assembly comprises a flexible puncture device 112 that comprises a mechanical puncture device 118. In some such embodiments, as shown in FIG. 1A the substantially flexible puncture device 112 comprises an energy based puncture device 114. In some embodiments, as shown in FIG. 1A, the needle assembly provides a substantially flexible puncture device 112 that comprises a substantially atraumatic tip (such as RF guidewire 10). In some embodiments, as shown in FIG. 1B, the substantially flexible puncture device comprises a relatively sharp (distal) tip 118*d*. In some embodiments, as shown in FIGS. 1A, 1B, and 3A-3B, the stiffening member comprises a reinforcing member 34.

In one broad aspect, embodiments of the present invention provide a transseptal system to facilitate a transseptal puncture procedure utilizing the inferior approach. The system involves converting a stiff energy based puncture device into: (i) a flexible energy delivery component for delivering RF energy such as an RF wire for puncturing using RF and (ii) a separate supporting member such as a reinforcing member for imparting structural and mechanical support to the assembly and to provide sufficient torque transfer to enable the RF wire to engage the septum and to facilitate advancement across the puncture site. As such, in some embodiments, the systems of the present provide an RF wire and a reinforcing member that are separate from and removable from one another to overcome the limitations associated with prior art needle based systems. In some such embodiments, the systems of the present invention provide a work flow that may reduce the number device exchanges, facilitate repeatability, provide adequate anchoring and enhance safety. Thus, in some embodiments, the system of the present invention provides a decoupled system that functionally decouples the energy delivery component and provides a flexible energy delivery component while providing structural support through a separate reinforcing member.

As an advantage, the reinforcing member is advanceable over the RF wire after positioning of the RF wire allowing the RF wire to function as an exchange wire to help eliminate the need for a separate exchange wire for gaining access into the heart. As such, the system enables a reduction in the number of device exchanges on the right side by using a flexible energy delivery component such an RF wire that provides exchange capabilities.

As an additional advantage, the reinforcing member may be advanced selectively when stiffness is required to complete aspects of the procedure for imparting structural and mechanical support to the assembly and to provide sufficient torque transfer to locate the fossa to enable the RF wire to engage the septum to create the puncture and to facilitate advancement/crossing to the left side after puncture. The reinforcing member is separate from the RF wire and additionally provides the advantage of allowing repositioning of the RF wire within the SVC to facilitate a repeat drop down procedure if necessary. More specifically, the reinforcing member can be removed partially or withdrawn partially while maintaining the RF wire within the right side of the heart. This eliminates exchange by eliminating the need for re-inserting an exchange wire, reducing procedural time and complexity. The RF wire can be repositioned within the SVC enabling the reinforcing member to be re-advanced over the RF wire to repeat the drop down procedure and to facilitate crossing after puncture.

As a further advantage, the system enables removal of the reinforcement member after puncture, enabling the energy delivery member, the RF wire to remain within the left atrium to facilitate anchoring within the left atrium, trackability and to provide safety while advancing into the left side.

Example 3 [Lockable Stylet and RF Guidewire]

As such some embodiments of the present invention provide a method is provided for carrying out a transseptal puncture, the method comprising: Advancing a J-wire into the superior vena cava; advancing a sheath and dilator over the wire into the superior vena cava; removing the J-wire; inserting a needle assembly comprising a stylet and RF guidewire within the dilator at a two finger position; dropping down from the superior vena cava into the heart to find the fossa; tenting with the dilator, advancing needle assembly to puncture position; puncturing and advancing the needle assembly until a stop within the dilator, holding the position and unlocking the RF guidewire; advancing the RF guidewire to anchor, crossing the sheath and dilator over the RF guidewire; and removing the stylet.

As such, in some embodiments, the systems of the present invention provide a work flow that may reduce the number device exchanges, facilitate repeatability, provide adequate anchoring and enhance safety.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. An assembly for puncturing tissue, the assembly comprising:
 a flexible puncturing wire for puncturing tissue, the flexible puncturing wire comprises
 an RF guidewire comprising a distal electrode tip; and
 a reinforced dilator including one or more polymer layers surrounding a hypotube selectively re-shapeable by a user to impart a desired curve to the reinforced dilator, the reinforced dilator supporting the flexible puncturing wire to enable force transmission to a distal end of the assembly;
 wherein the flexible puncturing wire is capable of being advanced within the reinforced dilator for puncturing tissue,
 wherein the flexible puncturing wire has a proximal portion having a proximal stiffness of between about 0.00107 $Nm^2$ and about 0.00179 $Nm^2$ and a distal portion, including the distal electrode tip, having a distal stiffness of between about $3.57 \times 10^{-6}$ $Nm^2$ and about $5.95 \times 10^{-6}$ $Nm^2$ such that the wire is usable independently from the reinforced dilator during another portion of the procedure to facilitate exchange and positioning of another device.

2. The assembly of claim 1, wherein the flexible puncturing wire comprises an energy delivery device that is operable to deliver energy for puncturing tissue.

3. The assembly of claim 1, wherein the hypotube is located between an inner polymer layer and an outer polymer layer.

4. The assembly of claim 1, wherein the reinforced dilator provides sufficient stiffness to the flexible puncturing wire when the flexible puncturing wire is inserted therein to enable torque to be transmitted to a distal end of the assembly.

5. The assembly of claim 1, wherein a curve portion of the reinforced dilator is shapeable to enable the curve portion to be re-shaped and to be reinserted therewith, in order to optimize the position of the assembly against a target tissue site.

6. The assembly of claim 1, wherein the reinforced dilator comprises a dilator radiopaque marker.

7. The assembly of claim 1, wherein the reinforced dilator comprises a radiopaque coil embedded within the one or more polymer layers at a distal tip thereof.

8. The assembly of claim 7, wherein the substantially flexible puncturing wire comprises:
 a device radiopaque marker at a distal end of thereof; and
 wherein the device radiopaque marker is configured to co-operate with the dilator radiopaque marker to indicate a relative position of the substantially flexible puncturing wire.

9. The assembly of claim 1, further comprising:
 a sheath for receiving the reinforced dilator for use therewith during a portion of the procedure.

10. The assembly of claim 9, wherein the assembly further comprises:
 a locking mechanism to enable axial and rotational coupling of the dilator with the sheath for a portion of the procedure.

11. The assembly of claim 10, wherein the dilator comprises a dilator hub and the sheath comprises a sheath hub, wherein the locking mechanism comprises one or more keys on the dilator hub for co-operatively engaging with the sheath hub.

12. The assembly of claim 8, wherein the assembly comprises:
 a first configuration, where the flexible puncturing wire is positionable within the reinforced dilator such that the device radiopaque marker is in alignment with the dilator radiopaque marker; and
 a second configuration, wherein the flexible puncturing wire is advanceable within the reinforced dilator such that the device radiopaque marker is out of alignment with and distal to the dilator radiopaque marker;
 wherein the second configuration indicates positioning of an energy delivery portion of the flexible puncturing wire beyond the reinforced dilator for positioning against a target tissue site for puncture of tissue.

13. The assembly of claim 1, wherein the RF guidewire comprises a pigtail wire.

14. The assembly of claim 4, wherein the reinforced dilator has a flexural rigidity of 0.0085 $Nm^2$ to 0.0145 $Nm^2$.

15. An assembly for puncturing tissue, the assembly comprising:
 a flexible puncturing wire for puncturing tissue; and
 a reinforced dilator including one or more polymer layers surrounding a hypotube selectively re-shapeable by a user to impart a desired curve to the reinforced dilator, the reinforced dilator supporting the flexible puncturing wire to enable force transmission to a distal end of the assembly and having a flexural rigidity of 0.0085 $Nm^2$ to 0.0145 $Nm^2$;
 wherein the flexible puncturing wire is capable of being advanced within the reinforced dilator for puncturing tissue,
 wherein the flexible puncturing wire has a proximal portion having a proximal stiffness of between about 0.00107 $Nm^2$ and about 0.00179 $Nm^2$ and a distal portion having a distal stiffness of between about $3.57 \times 10^{-6}$ $Nm^2$ and about $5.95 \times 10^{-6}$ $Nm^2$ such that the wire is usable independently from the reinforced dilator during another portion of the procedure to facilitate exchange and positioning of another device, and
 wherein a locking mechanism enables axial and rotational coupling of the dilator with a sheath for a portion of the procedure.

16. The assembly of claim 15, wherein the dilator comprises a dilator hub and the sheath comprises a sheath hub, wherein the locking mechanism comprises one or more keys on the dilator hub for co-operatively engaging with the sheath hub.

17. An assembly for puncturing tissue, the assembly comprising:
 a flexible puncturing wire for puncturing tissue, the flexible puncturing wire comprises an RF guidewire comprising a distal electrode tip and a device radiopaque marker at a distal end thereof; and
 a reinforced dilator including one or more polymer layers surrounding a hypotube selectively re-shapeable by a user to impart a desired curve to the reinforced dilator, the reinforced dilator supporting the flexible puncturing wire to enable force transmission to a distal end of the assembly and having a flexural rigidity of 0.0085 $Nm^2$ to 0.0145 $Nm^2$;

wherein the flexible puncturing wire is capable of being advanced within the reinforced dilator for puncturing tissue, wherein the flexible puncturing wire has a proximal portion having a proximal stiffness of between about 0.00107 $Nm^2$ and about 0.00179 $Nm^2$ and a distal portion, including the distal electrode tip, having a distal stiffness of between about $3.57 \times 10^{-6}$ $Nm^2$ and about $5.95 \times 10^{-6}$ $Nm^2$ such that the wire is usable independently from the reinforced dilator during another portion of the procedure to facilitate exchange and positioning of another device.

18. The assembly of claim 17, wherein the device radiopaque marker is configured to co-operate with a dilator radiopaque marker at a distal tip of the reinforced dilator to indicate a relative position of the flexible puncturing wire.

19. The assembly of claim 18, wherein the assembly comprises:

a first configuration, where the flexible puncturing wire is positionable within the reinforced dilator such that the device radiopaque marker is in alignment with the dilator radiopaque marker; and a second configuration, wherein the flexible puncturing wire is advanceable within the reinforced dilator such that the device radiopaque marker is out of alignment with and distal to the dilator radiopaque marker;

wherein the second configuration indicates positioning of an energy delivery portion of the flexible puncturing wire beyond the reinforced dilator for positioning against a target tissue site for puncture of tissue.

20. The assembly of claim 15, wherein the reinforced dilator comprises a dilator hub and the sheath comprises a sheath hub, wherein a locking mechanism comprises one or more keys on the dilator hub for co-operatively engaging with the sheath hub and enables axial and rotational coupling of the dilator with a sheath for a portion of the procedure.

* * * * *